US010626149B2

(12) United States Patent
Lico et al.

(10) Patent No.: US 10,626,149 B2
(45) Date of Patent: Apr. 21, 2020

(54) VIRAL CHIMERIC PARTICLE OF POTATO VIRUS X AND USE THEREOF FOR IN VITRO DIAGNOSIS OF SJÖGREN SYNDROME

(71) Applicants: ENEA-AGENZIA NAZIONALE PER LE NUOVE TECNOLOGIE, L'ENERGIA E LO SVILUPPO ECONOMICO SOSTENIBILE, Rome (IT); UNIVERSITA' DEGLI STUDI DI VERONA, Verona (IT)

(72) Inventors: Chiara Lico, Rome (IT); Selene Baschieri, Rome (IT); Eugenio Benvenuto, Rome (IT); Linda Avesani, Verona (IT); Elisa Tinazzi, Verona (IT); Elena Bartoloni Bocci, Perugia (IT); Mario Pezzotti, Verona (IT); Claudio Lunardi, Verona (IT)

(73) Assignees: ENEA-AGENZIA NAZIONALE PER LE NUOVE TECNOLOGIE, L'ENERGIA E LO SVILUPPO ECONOMICO SOSTENIBILE, Rome (IT); UNIVERSITA' DEGLI STUDI DI VERONA, Verona (IT)

( * ) Notice: Subject to any disclaimer, the term of this patent is extended or adjusted under 35 U.S.C. 154(b) by 0 days.

(21) Appl. No.: 15/579,150

(22) PCT Filed: Jun. 3, 2016

(86) PCT No.: PCT/IT2016/000146
§ 371 (c)(1),
(2) Date: Dec. 1, 2017

(87) PCT Pub. No.: WO2016/194014
PCT Pub. Date: Dec. 8, 2016

(65) Prior Publication Data

US 2018/0170970 A1 Jun. 21, 2018

(30) Foreign Application Priority Data

Jun. 3, 2015 (IT) ........................ 102015000020005

(51) Int. Cl.

| | |
|---|---|
| ***C07K 14/005*** | (2006.01) |
| ***C12N 7/00*** | (2006.01) |
| ***C07K 14/47*** | (2006.01) |
| ***C07K 14/08*** | (2006.01) |
| ***C12N 7/04*** | (2006.01) |
| ***G01N 33/569*** | (2006.01) |

(52) U.S. Cl.
CPC ............ *C07K 14/005* (2013.01); *C07K 14/08* (2013.01); *C07K 14/47* (2013.01); *C12N 7/00* (2013.01); *C12N 7/045* (2013.01); *G01N 33/56983* (2013.01); *C07K 2319/00* (2013.01); *C12N 2770/40022* (2013.01)

(58) Field of Classification Search
None
See application file for complete search history.

(56) References Cited

FOREIGN PATENT DOCUMENTS

WO WO 2013/174783 A1 11/2013

OTHER PUBLICATIONS

Navone et al. (Journal of Autoimmunity, 2005, p. 229-234).*
Lico et al. (Vaccine, 2009, p. 5069-5076).*
Flower et al., "Structure and sequence relationships in the lipocalins and related proteins," Protein Science, May 1, 1993, pp. 753-761, vol. 2, No. 5, Cambridge University Press, US.
International Search Report and Written Opinion issued in PCT/IT2016/000146 dated Sep. 15, 2016.
Italian Search Report and Written Opinion issued in ITUB20151199 dated Feb. 2, 2016.
Lico et al., "Plant-produced potato virus X chimeric particles displaying an influenza virus-derived peptide activate specific CD8+ T cells in mice," Vaccine, Aug. 13, 2009, pp. 5069-5076, vol. 27. No. 37, Elsevier Ltd., GB.
Marusic et al., "Chimeric Plant Virus Particles as Immunogens for Inducing Murine and Human Immune Responses against Human Immunodeficiency Virus Type 1," Journal of Virology, Sep. 1, 2001, pp. 8434-8439, vol. 75, No. 18, The American Society for Microbiology, US.
Navone et al., "Identification of tear lipocalin as a novel autoantigen target in Sjögren's syndrome," Journal of auto immunity, Nov. 1, 2005, pp. 229-234, vol. 25, No. 3, London, GB.
Tinazzi et al., "Plant-Derived Chimeric Virus Particles for the Diagnosis of Primary Sjögren Syndrome," Frontiers in Plant Science, Dec. 1, 2015, pp. 1-11, vol. 6, No. 1080.

* cited by examiner

*Primary Examiner* — Agnieszka Boesen
(74) *Attorney, Agent, or Firm* — Arent Fox LLP

(57) ABSTRACT

The present invention relates to a chimeric virus particle of potato virus X, said particle having, as a capsid protein, a fusion protein containing a capsid protein and an antigenic determinant of lipocalin, and the use thereof in the in vitro diagnosis of Sjögren's Syndrome using the ELISA method.

6 Claims, 7 Drawing Sheets

Specification includes a Sequence Listing.

```
CLUSTAL 2.1 Multiple sequence alignment

CPPVX-CC    ATGT-------------------------------------------------------- 4
CPPVX-wt    ATGTCAGCACCAGCTAGCACAACACAGCCCATAGGGTCAACTACCTCAACTACCACAAAA 60
            ****

CPPVX-CC    -------GTGCCACTCCTGCCACAGCTTCAGGCCTGTTCACCATCCCGGATGGGGATTTC 57
CPPVX-wt    ACTGCAGGCGCAACTCCTGCCACAGCTTCAGGCCTGTTCACCATCCCGGATGGGGATTTC 120
                   * ** ************************************************

CPPVX-CC    TTTAGTACAGCCCGTGCCATAGTAGCCAGCAATGCTGTCGCAACAAATGAGGACCTCAGC 117
CPPVX-wt    TTTAGTACAGCCCGTGCCATAGTAGCCAGCAATGCTGTCGCAACAAATGAGGACCTCAGC 180
            ************************************************************

CPPVX-CC    AAGATTGAGGCTATTTGGAAGGACATGAAGGTGCCCACAGACACTATGGCACAGGCTGCT 177
CPPVX-wt    AAGATTGAGGCTATTTGGAAGGACATGAAGGTGCCCACAGACACTATGGCACAGGCTGCT 240
            ************************************************************

CPPVX-CC    TGGGACTTAGTCAGACACTGTGCTGATGTAGGATCATCCGCTCAAACAGAAATGATAGAT 237
CPPVX-wt    TGGGACTTAGTCAGACACTGTGCTGATGTAGGATCATCCGCTCAAACAGAAATGATAGAT 300
            ************************************************************

CPPVX-CC    ACAGGTCCCTATTCCAACGGCATCAGCAGAGCTAGACTGGCAGCAGCAATTAAAGAGGTG 297
CPPVX-wt    ACAGGTCCCTATTCCAACGGCATCAGCAGAGCTAGACTGGCAGCAGCAATTAAAGAGGTG 360
            ************************************************************

CPPVX-CC    TGCACACTTAGGCAATTTTGCATGAAGTATGCTCCAGTGGTATGGAACTGGATGTTAACT 357
CPPVX-wt    TGCACACTTAGGCAATTTTGCATGAAGTATGCTCCAGTGGTATGGAACTGGATGTTAACT 420
            ************************************************************

CPPVX-CC    AACAACAGTCCACCTGCTAACTGGCAAGCACAAGGTTTCAAGCCTGAGCACAAATTCGCT 417
CPPVX-wt    AACAACAGTCCACCTGCTAACTGGCAAGCACAAGGTTTCAAGCCTGAGCACAAATTCGCT 480
            ************************************************************

CPPVX-CC    GCATTCGACTTCTTCAATGGAGTCACCAACCCAGCTGCCATCATGCCCAAAGAGGGGCTC 477
CPPVX-wt    GCATTCGACTTCTTCAATGGAGTCACCAACCCAGCTGCCATCATGCCCAAAGAGGGGCTC 540
            ************************************************************

CPPVX-CC    ATCCGGCCACCGTCTGAAGCTGAAATGAATGCTGCCCAAACTGCTGCCTTTGTGAAGATT 537
CPPVX-wt    ATCCGGCCACCGTCTGAAGCTGAAATGAATGCTGCCCAAACTGCTGCCTTTGTGAAGATT 600
            ************************************************************

CPPVX-CC    ACAAAGGCCAGGGCACAATCCAACGACTTTGCCAGCCTAGATGCAGCTGTCACTCGAGGT 597
CPPVX-wt    ACAAAGGCCAGGGCACAATCCAACGACTTTGCCAGCCTAGATGCAGCTGTCACTCGAGGT 660
            ************************************************************

CPPVX-CC    CGTATCACTGGAACAACAACCGCTGAGGCTGTTGTCACTCTACCACCACCATAA 651
CPPVX-wt    CGTATCACTGGAACAACAACCGCTGAGGCTGTTGTCACTCTACCACCACCATAA 714
            ******************************************************
```

Fig. 5

CLUSTAL 2.1 Multiple sequence alignment

```
CPPVX-CC      ---------------------MCATPATASGLFTIPDGDFFSTARAIVASNAVATNEDLS 39
CPPVX-Sma     ---------------------MPGTPATASGLFTIPDGDFFSTARAIVASNAVATNEDLS 39
CPPVX-wt      MSAPASTTQPIGSTTSTTTKTAGATPATASGLFTIPDGDFFSTARAIVASNAVATNEDLS 60
                                     .************************************

CPPVX-CC      KIEAIWKDMKVPTDTMAQAAWDLVRHCADVGSSAQTEMIDTGPYSNGISRARLAAAIKEV 99
CPPVX-Sma     KIEAIWKDMKVPTDTMAQAAWDLVRHCADVGSSAQTEMIDTGPYSNGISRARLAAAIKEV 99
CPPVX-wt      KIEAIWKDMKVPTDTMAQAAWDLVRHCADVGSSAQTEMIDTGPYSNGISRARLAAAIKEV 120
              ************************************************************

CPPVX-CC      CTLRQFCMKYAPVVWNWMLTNNSPPANWQAQGFKPEHKFAAFDFFNGVTNPAAIMPKEGL 159
CPPVX-Sma     CTLRQFCMKYAPVVWNWMLTNNSPPANWQAQGFKPEHKFAAFDFFNGVTNPAAIMPKEGL 159
CPPVX-wt      CTLRQFCMKYAPVVWNWMLTNNSPPANWQAQGFKPEHKFAAFDFFNGVTNPAAIMPKEGL 180
              ************************************************************

CPPVX-CC      IRPPSEAEMNAAQTAAFVKITKARAQSNDFASLDAAVTRGRITGTTTAEAVVTLPPP 216
CPPVX-Sma     IRPPSEAEMNAAQTAAFVKITKARAQSNDFASLDAAVTRGRITGTTTAEAVVTLPPP 216
CPPVX-wt      IRPPSEAEMNAAQTAAFVKITKARAQSNDFASLDAAVTRGRITGTTTAEAVVTLPPP 237
              *********************************************************
```

Fig. 6

```
CLUSTAL 2.1 Multiple sequence alignment

CPPVX-CC      ATGTGTGCCACTCCTGCCACAGCTTCAGGCCTGTTCACCATCCCGGATGGGGATTTCTTT 60
CPPVX-Sma     ATGCCCGGGACTCCTGCCACAGCTTCAGGCCTGTTCACCATCCCGGATGGGGATTTCTTT 60
              ***    *  *************************************************

CPPVX-CC      AGTACAGCCCGTGCCATAGTAGCCAGCAATGCTGTCGCAACAAATGAGGACCTCAGCAAG 120
CPPVX-Sma     AGTACAGCCCGTGCCATAGTAGCCAGCAATGCTGTCGCAACAAATGAGGACCTCAGCAAG 120
              ************************************************************

CPPVX-CC      ATTGAGGCTATTTGGAAGGACATGAAGGTGCCCACAGACACTATGGCACAGGCTGCTTGG 180
CPPVX-Sma     ATTGAGGCTATTTGGAAGGACATGAAGGTGCCCACAGACACTATGGCACAGGCTGCTTGG 180
              ************************************************************

CPPVX-CC      GACTTAGTCAGACACTGTGCTGATGTAGGATCATCCGCTCAAACAGAAATGATAGATACA 240
CPPVX-Sma     GACTTAGTCAGACACTGTGCTGATGTAGGATCATCCGCTCAAACAGAAATGATAGATACA 240
              ************************************************************

CPPVX-CC      GGTCCCTATTCCAACGGCATCAGCAGAGCTAGACTGGCAGCAGCAATTAAAGAGGTGTGC 300
CPPVX-Sma     GGTCCCTATTCCAACGGCATCAGCAGAGCTAGACTGGCAGCAGCAATTAAAGAGGTGTGC 300
              ************************************************************

CPPVX-CC      ACACTTAGGCAATTTTGCATGAAGTATGCTCCAGTGGTATGGAACTGGATGTTAACTAAC 360
CPPVX-Sma     ACACTTAGGCAATTTTGCATGAAGTATGCTCCAGTGGTATGGAACTGGATGTTAACTAAC 360
              ************************************************************

CPPVX-CC      AACAGTCCACCTGCTAACTGGCAAGCACAAGGTTTCAAGCCTGAGCACAAATTCGCTGCA 420
CPPVX-Sma     AACAGTCCACCTGCTAACTGGCAAGCACAAGGTTTCAAGCCTGAGCACAAATTCGCTGCA 420
              ************************************************************

CPPVX-CC      TTCGACTTCTTCAATGGAGTCACCAACCCAGCTGCCATCATGCCCAAAGAGGGGCTCATC 480
CPPVX-Sma     TTCGACTTCTTCAATGGAGTCACCAACCCAGCTGCCATCATGCCCAAAGAGGGGCTCATC 480
              ************************************************************

CPPVX-CC      CGGCCACCGTCTGAAGCTGAAATGAATGCTGCCCAAACTGCTGCCTTTGTGAAGATTACA 540
CPPVX-Sma     CGGCCACCGTCTGAAGCTGAAATGAATGCTGCCCAAACTGCTGCCTTTGTGAAGATTACA 540
              ************************************************************

CPPVX-CC      AAGGCCAGGGCACAATCCAACGACTTTGCCAGCCTAGATGCAGCTGTCACTCGAGGTCGT 600
CPPVX-Sma     AAGGCCAGGGCACAATCCAACGACTTTGCCAGCCTAGATGCAGCTGTCACTCGAGGTCGT 600
              ************************************************************

CPPVX-CC      ATCACTGGAACAACAACCGCTGAGGCTGTTGTCACTCTACCACCACCATAA 651
CPPVX-Sma     ATCACTGGAACAACAACCGCTGAGGCTGTTGTCACTCTACCACCACCATAA 651
              ***************************************************
```

Fig. 7

VIRAL CHIMERIC PARTICLE OF POTATO VIRUS X AND USE THEREOF FOR IN VITRO DIAGNOSIS OF SJÖGREN SYNDROME

CROSS-REFERENCE TO RELATED APPLICATIONS

This application is a National Stage entry of International Application No.: PCT/IT2016/000146, filed Jun. 3, 2016, which claims priority to Italian Patent Application No. 102015000020005, filed Jun. 3, 2015. The disclosure of the priority applications are hereby incorporated in their entirety by reference.

The present invention relates to a chimeric virus particle of potato virus X and use thereof in the in vitro diagnosis of Sjögren's Syndrome.

In greater detail, the invention relates to a chimeric virus particle of potato virus X, said particle having fused to its capsid protein a lipocalin-derived autoantigenic determinant associated with Sjögren's Syndrome, and the use thereof in the in vitro diagnosis of the Sjögren's Syndrome, for example using the ELISA method.

Sjögren's Syndrome (SS) is an autoimmune disease with an incidence of 0.6% in the general population and a female:male ratio of 9:1. The disease manifests itself early with involvement of the exocrine glands, above all the salivary and lachrymal glands, resulting in xerostomia and xerophthalmia. The systemic manifestations, characterized by organ involvement at a cutaneous, articular, pulmonary, renal, pancreatic and neurological level are generally less frequent and appear later, although in a percentage ranging between 25 and 92% of cases neurological involvement can represent the initial symptom.

In consideration of the different visceral and non-visceral organ involvement, SS can manifest itself with extremely different symptoms, and with extremely heterogeneous involvement and degree of disability. Some patients, in fact, can present with an isolated glandular involvement, with xerostomia and xerophthalmia ranging from mild to severe, when the gland insufficiency and loss of the saliva and/or tear secretion function lead to extreme consequences, such as swelling and parotid pain, extreme dryness of the mouth with aphthous ulcers, dysphagia variably associated with oral cavity infections, as well as a major alteration of the visus with photophobia, pain and a condition of blepharitis and/or keratitis which eventually leads to opacification and corneal ulceration. Systemic involvement can be characterized by cutaneous involvement, first of all Raynaud's phenomenon, but also purpura or urticarial vasculitis; musculoskeletal involvement, characterized by arthromyalgia or arthritis, generally symmetrical and rarely of an erosive character; pulmonary involvement, with coughing and/or secondary dyspnea, dry tracheobronchitis or interstitiopathy; or renal involvement ranging from an asymptomatic tubular dysfunction with tubular acidosis to kidney failure with a possible outcome also requiring dialysis treatment. The involvement of the gastrointestinal tract is also variable, with possible autoimmune pancreatitis, or association with autoimmune conditions such as atrophic gastritis, celiac disease, primitive biliary cirrhosis or autoimmune hepatitis, with the consequent associated set of symptoms, as well as neurological involvement, generally tied to sensory or more infrequently motor peripheral neuropathies, with allodynia or hyperalgesia, paresthesias and proprioceptive disorders, or less frequently to central forms, which are, however, associated with a greater degree of disability, as in the case of cerebral vasculitis, cerebellar syndromes, and memory lapses, or even manifest forms of dementia or transverse myelitis.

As a result of its multi-faceted and variably disabling clinical manifestations, many aspects of the etiopathogenesis of the disease are still unknown, as in the case of a large part of autoimmune disorders, though there is known to be an interaction between genetic susceptibility—in particular as regards both histocompatibility complex class II genes and non-HLA genes—and triggering environmental factors, primarily infectious agents, capable of setting off an inflammatory process which is characterized by immune system auto-aggression against specific target structures, with the autoimmune process subsequently becoming chronic, resulting in tissue damage (Lee et al. 2009).

Both T lymphocytes and B lymphocytes are involved in the pathogenesis of the SS and in the tissue damage that characterizes it. In particular, Th1, Th2 and Th17 cells as well as B cells are involved in the different stages characterizing the natural history of the pathology, from the pre-clinical stage to the stage of clinical expression with clear and manifest symptoms. In SS, Th1 cells release interferon gamma (IFNγ), regulate cell-mediated immunity, and play a role in delaying cell maturation by influencing the organogenesis of salivary glands and the expression of cellular antigens, with a consequent loss of self-tolerance. Th2 cells release interleukin 4 (IL-4), which is fundamental in the early stage of the adaptive immune response, in particular, for isotype switching of immunoglobulin (Ig) and the consequent synthesis of pathogenetic IgG1 autoantibodies (Lee et al. 2009). Th17 cells make up a particular subset of memory CD4 cells, capable of secreting cytokines with a powerful pro-inflammatory activity belonging to the IL 17 family (Bettelli et al. 2008). In view of the complexity of the interactions between cell and cytokine patterns induced by environmental stimuli and involved in the pathogenesis of SS, Lee et al. (2009) have hypothesized that the disease develops in three different successive stages, two of which preclinical, i.e. asymptomatic and silent, and a clinical stage. In the first stage one observes a prevalent involvement of the Th1/IFNγ system characterized by delayed organogenesis of the salivary glands, delayed expression of antigens on the surface of acinar cells, with a consequent loss of the clonal deletion of B and T cells, a loss of self-tolerance and an increased expression of aberrant proteins and cell apoptosis. This is followed, in the second preclinical stage (i.e. silent for the patient and mediated by Th2 and Th17 lymphocytes and B lymphocytes) by an increased expression of numerous epitopes at the glandular level, with the appearance of a major leukocyte infiltration, the triggering of an autoreactive local immune response and the onset of active autoantibody synthesis. The effects of these phenomena culminate in the third stage, in which the autoimmune process gives rise to clinically evident functional damage, which is expressed through a reduction in exocrine secretion from the gland tissue involved, with the consequent clinical symptoms.

Multiple autoantibodies are produced during the course of SS: some of them have a diagnostic value, others are predictive of possible organ damage, and still others have a prognostic or unclear value. ANA positivity, mostly with a speckled pattern, anti-ENA Ro/SSA and La/SSB, anti-salivary duct cell antibodies, anti-thyroid antibodies, anti-gastric parietal cell antibodies and antimitochondrial antibodies frequently occur. High titles of anti-α-fodrin, anti-muscarinic receptors type 3, anti-carbonic anhydrase II and anti-proteasome antibodies have also been described. Recently, some authors have also described high titles of anti-lipocalin antibodies (Navone et al. 2005), lipocalin being a protein that demonstrates a high sequence homology with α-fodrin as well as with the early protein D of EBV (Epstein-Barr Virus), which seems to confirm it to be a potential environmental agent triggering the disease in genetically predisposed subjects. Given the close association between EBV and SS, also in relation to the high sequence homology that has been demonstrated between a protein epitope of that virus and two autoantigens of relevance in the disease itself, it is interesting to evaluate their pathogenetic role and diagnostic potential.

Within the field of autoimmune diseases, due to the complex, variegated array of symptoms, as well as the presence of different laboratory and/or instrumental data, the diagnosis is often based on a global assessment of the situation and the criteria for classifying the disease are often used to support the diagnosis itself. Classification criteria in fact represent objective diagnostic parameters, which are fundamental to assure the standardization of patients who are included in clinical studies, facilitate the analysis and render the results of different clinical studies comparable, as well as enabling a comparison among patients referred to different clinical facilities.

With regard to the diagnosis of SS, the classification criteria still most widely used today are the AECG (American European Consensus Group) criteria of 2002 (Vitali et al. 2002), which are based on an assessment of 6 phenomena, namely: I) ocular symptoms (symptoms of dry eyes for over 3 months or use of artificial tears for over 3 months); II) oral symptoms (dry mouth for at least 3 months or recurrent or persistently swollen salivary glands or need for liquids to swallow solid foods); III) ocular signs (abnormal Shirmer's test or Rose Bengal/fluorescein staining); IV) histopathological characteristics with a focus score ≥1 on biopsy of the minor salivary glands; V) reduction in salivation, documented by salivary flow measurement or indirectly with parotid scialography or salivary gland scintigraphy; and VI) presence of autoantibodies (anti-ENA SSA/Ro and/or SSB/La positivity).

Based on AECG criteria, in order to formulate a diagnosis of SS it is necessary for at least 4 of the 6 criteria listed above to be met, including necessarily the histopathological criterion or presence of autoantibodies, and at least 3 of the 4 objective criteria. Given the large differences between the two procedures (biopsy and serological analysis) in terms of cost and invasiveness, in clinical practice, where the other criteria established by the AECG (dry eye and dry mouth, appropriately measured) are met, a serological analysis is performed first and only in the event that the latter is negative will a salivary gland biopsy follow.

In 2012, new ACR (American College of Rheumatology) classification criteria were introduced (Shiboski et al. 2012), which, compared to the AECG criteria, introduce a simplification of the procedure, it being necessary for only 2 of the 3 objective criteria identified to be met. The criteria to be met are: I) ocular signs (fluorescein staining with a score ≥3); II) histopatological characteristics with a focus score ≥1 on minor salivary gland biopsy; III) presence of autoantibodies (positive anti-ENA SSA/Ro and/or SSB/La or alternatively positive rheumatoid factor or ANA with a title ≥1:320).

Unlike the AECG criteria, the ACR criteria do not take into consideration either the subjective symptoms of the patient (presence of xerostomia/xerophthalmia) or functional assessments regarding the major salivary glands (salivary flow measurement, scialography or scintigraphy), but only an evaluation of ocular involvement with a test of a qualitative type and the presence of a broader spectrum of autoantibodies, in particular ANA, which is positive in a percentage of patients ranging from 60 to 85% of the cases (Nardi et al. 2006), as compared to what has been documented for anti-ENA SSA/Ro or anti-ENA SSB/La, equal, respectively, to 52-67% or 49% (Routsias et al. 2007). These criteria no doubt enable the recognition of subjects with SS at an earlier stage; specifically, they also enable the subset of subjects negative for anti-ENA SSA/Ro or anti-ENA SSB/La (about 50% of affected subjects) to be diagnosed with the disease. However, they have not yet been validated in a large number of European case studies and, moreover, the AECG criteria of 2002, though more stringent, still demonstrate higher specificity (AECG criteria Sp 90.4% versus ACR criteria Sp 83.5%; Comec et al. 2014) and are therefore still more widely used.

For the sake of completeness, given that the diagnostic criteria, as opposed to the classification criteria, also depend on information derived from the patient's medical history, a global assessment of the patient's laboratory and instrumental data, as well as the clinician's experience, it is worth noting the existence of a subgroup of patients who are negative for autoantibodies (i.e. ANA, anti-ENA SSA/Ro and anti-ENA SSB/La negative), but have strongly suggestive overall clinical, laboratory and instrumental data and a salivary gland histology which support the diagnosis of the pathology. In particular, for this subset of patients, it is essential to find new diagnostic markers which may serve to identify also the affected individuals in whom the diagnosis has been ruled out due to the absence of the currently available markers. It has recently been proposed to assay anti-α-fodrin antibodies as markers of the pathology: until now, the usefulness of this assay has been confirmed only as validation of the diagnosis in the presence of anti-ENA SSA/Ro or anti-ENA SSB/La (Qin et al. 2014).

With regard to new diagnostic markers for the diagnosis of SS, the presence of autoantibodies against human tear lipocalin has recently been demonstrated in the serum of subjects suffering from SS.

Tear lipocalin, together with lysozyme and lactoferrin, is the protein most largely represented in human tears, but it is also produced by von Ebner's glands, in the nasal mucosa, in the tracheobronchial mucosa and at the level of the prostate. It belongs to the family of lipocalins, low-molecular-weight proteins characterized by an ability to bind small hydrophobic molecules, complex with other soluble macromolecules to form macro complexes, and bind to specific receptors exposed on the cell surface to mediate the transduction and internalization of a signal. Tear lipocalin binds various ligands, including phospholipids, fatty acids, alcohols, glycolipids and cholesterol, and has a function that is closely associated with the role of its ligands. It prevents tear evaporation by binding fatty acids and phospholipids, maintains corneal integrity through a barrier function, again by virtue of the bond with the lipid components of tears, and performs an anti-microbial action, in particular an anti-fungal one (Gachon et al. 1998). Lipocalin also has the function of an enzyme and enzymatic inhibitor; it represents, in fact, the main tear endonuclease and has an inhibitory activity on cysteine-proteinase (Glasgow et al. 2011). A reduction in tear lipocalin has been suggested in all diseases with reduced tear secretion; moreover, recent studies have demonstrated that the concentration thereof is significantly reduced during the course of SS, whereas in the case of dry-eye syndrome in the post-menopausal age, as well as in situations of keratoconjunctivitis sicca not associated with SS, the concentration of tear lipocalin shows to be substantially comparable to that present in the tears of control subjects (Caffery et al. 2008).

As noted above, the presence of autoantibodies against human tear lipocalin in the serum of subjects suffering from SS has recently been demonstrated (Navone et al. 2005), confirming the close association between tear lipocalin and the pathology. Titles of these antibodies are not detectable in the serum of control subjects or patients with other autoimmune pathologies such as rheumatoid arthritis or LES, which confirms the selective link between the protein itself and the disease.

The recognition of lipocalin as a potential autoantigen for SS was based on the screening of a peptide library, with the use of random peptide sequences tested with the serum of patients suffering from the pathology of interest, SS in this specific case (Navone et al. 2005). This method served to reveal a synthetic dodecapeptide sequence, called Sjögren's peptide (GDRDAGSRGLVS (SEQ ID NO:1)), with a high sequence homology with tear lipocalin (FEKAAGARGLST (SEQ ID NO:2) and α-fodrin, as well as with the D protein antigen of EBV. This homology was validated both by means of an ELISA test with affinity purified antibodies from the serum of patients with SS, and using the immunoprecipitation of lipocalin from a cell lysate and tears, respectively tested with purified antibodies from patients and commercial anti-lipocalin antibodies. It was thus hypothesized that, in genetically predisposed subjects, via a mechanism of molecular mimicry, EBV infection or reactivation of EBV infection may induce an increase in the production of α-fodrin degradation fragments, as an effect of the immune response against the EBV early antigen D, with a consequent alteration of this cytoskeletal protein, already known as an important autoantigen during the course of SS (Qin et al. 2014). The anti-EBV D antigen antibodies also appear to bind tear lipocalin, leading to a functional modification thereof, as well as a reduction in gland secretion, with obvious clinical consequences.

ELISA (Enzyme-Linked Immunosorbent Assay) is a method which makes it possible to ascertain the presence of antibodies specific for a given antigen in the serum of patients suffering from the pathology of interest. In the case of SS, identifying an autoantigen sensitive and specific for the disease is of considerable interest, as there is undoubtedly a portion of patients who are diagnosed late or not diagnosed with the disease based on negative results for anti-ENA SSA/Ro or anti-ENA SSB/La or, using the more recent ACR criteria, ANA. From this perspective, as mentioned above, tear lipocalin demonstrates to be a molecule of considerable interest, given both the close association the molecule has with the pathology (Caffery et al. 2008) and its demonstrated pathogenetic role in triggering the disease following an EBV infection or reactivation of EBV infection (Navone et al. 2005). As previously described, the lipocalin peptide (LIP peptide) obtained by chemical synthesis has already been used to test sera obtained from control subjects and subjects with autoimmune diseases, including SS, rheumatoid arthritis, LES and scleroderma, precisely with the aim of validating its diagnostic sensitivity and specificity, and it has demonstrated to be a potential autoantigen of significant diagnostic value.

However, an ELISA based on the use solely of the peptide obtained by chemical synthesis is not completely reliable, as the small dimensions and physicochemical characteristics of the peptide itself cannot guarantee adhesion to the polystyrene of the plate used for the test, impairing its reproducibility and effectiveness. In particular, notwithstanding the use of highly specific polystyrene plates for binding small peptides, the result obtained with experiments in triplicate has not always proven to be reproducible and, in the case of some lots of plates, not usable, given that the data obtained from the reaction between the synthetic LIP peptide and the serum showed a lower value than the absorbance of the substrate alone, used as the internal experimental control of the system (the so-called reference blank).

In light of the above, there is an evident need to be able to have new methods for diagnosing SS which can overcome the disadvantages of the known methods.

The potato virus X (PVX) belongs to the family Alphaflexiviridae and genus Potexvirus. It is a filamentous and flexible rod-like virus, with an average length of 500 nm and a diameter of about 13 nm. Its genome consists of a positive-sense single-stranded RNA molecule 6435 bases long (for the strain X3, which is the one of reference in this case; Accession Number D00344) and codes for 5 different proteins: an RNA-dependent RNA polymerase (RdRp, replicase), three viral movement proteins, identified as p8, p12 and p25 (or also proteins of the Triple Gene Block, TGBp1, TGBp2 and TGBp3, respectively) and the viral coat protein (CP) (FIG. 1). With the exception of the replicase gene, the expression of the open reading frames (ORFs) is regulated by the activity of several specific subgenomic promoters. The genome is 5' capped (i.e. it has a methylguanosine cap, m7GpppG) and 3' polyadenylated (it has a polyA tail). The completely assembled virion consists of a molecule of RNA totally surrounded by about 1300 identical copies of CP, which are associated to form a spiral around the viral nucleic acid with a progressive process. This is why in vivo, during replication inside the plant cell, virions of different lengths corresponding to the different stages of progress in the assembly can be identified. During purification, however, the protocol adopted makes it possible to obtain a preparation of particles that are homogeneous in length and have an expected size of 500 nm. The host of choice of the virus is the potato plant, *Solanum tuberosum*, but PVX is capable of replicating and infecting plants belonging to the family Solanaceae in general, including plants belonging to the genus *Nicotiana*, and in particular *N. benthamiana*, an amphitetraploid herbaceous plant (2n=4x=38) native to western Australia and by now widely used as a model plant in plant virology experiments and in the transient expression of heterologous proteins.

The virus travels from the inoculation site via a cell-to-cell movement; then it reaches the phloem vessels, through which it moves into the leaves of the phytomers above the ones where inoculation took place. The typical symptoms it produces are chlorotic and then necrotic spots corresponding to the individual loci of infection on inoculated leaves, and a diffuse chlorotic mosaic accompanied by leafroll in systemically infected leaves.

An approach commonly used in molecular farming to produce peptides is to genetically fuse the sequence of interest to the gene encoding the CP of plant viruses. In the case of PVX in particular, this takes place by fusion at the 5' of the gene, i.e. the N-terminal end of the corresponding protein. In this manner, when the CP is translated it will be chimeric, i.e. bear an additional portion, and when assembled in the mature virion it will produce chimeric virus particles (CVPs) which will expose the heterologous portion on the surface of the virus (FIG. 2*b*).

Following the viral infection, samples of the symptomatic systemic tissue are taken and the CVPs are purified and used in the planned experiments.

The entire PVX genome has been cloned, in the form of cDNA, in an expression vector for plant cells called plasmid pPVX201 (Baulcombe et al. 1995; FIG. 3; see SEQ ID NO:3 in the appended list of the sequences; see also http://www.plantsci.cam.ac.uk/research/davidbaulcombelmethods/pvx-expression-vectors/sequences).

The vector consists of: the strong constitutive promoter 35S derived from the cauliflower mosaic virus, placed upstream of the PVX cDNA; and the NOS terminator derived from the nopaline synthase gene of *Agrobacterium tumefaciens*, placed downstream of the PVX cDNA. These two regions constitute the portions of the vector that regulate the expression of the viral genome inside the plant cell. Among its most relevant elements, the plasmid also has an origin of bacterial replication and the beta-lactamase gene, which lends it resistance to the antibiotic ampicillin; this is useful for the selection of correctly transformed bacterial clones. In this vector, moreover, a single multi-cloning site (MCS) is inserted upstream of the CP gene for the insertion of additional ORFs, along with a duplicated copy of the subgenomic promoter of the CP, which has the function of directing the expression of the additional ORF inserted by cloning in the MCS.

Thanks to this plasmid, which enables the viral genome to be easily modified, PVX has been widely used as an expression vector, in plants, of heterologous proteins, mostly ones of pharmaceutical-biomedicinal interest, but not limited to these. In this approach, the sequence coding for the protein of interest is inserted in the MCS and the recombinant plasmid thus obtained is used for direct inoculation into the leaves of the plant of interest. Inside its cells, the 35S promoter will start replication of the viral genome with the production of a RNA copy of the viral cDNA and the translation of the first protein, RdRp. From this moment, the viral RNA polymerase will guide the production of subgenomic RNAs and other viral proteins, together with the heterologous protein of interest, which will be produced free inside the cell cytoplasm. Alternatively, with another procedure, described in detail below, the sequence of interest can be fused to the coat protein of the virus.

With the above-mentioned method, a chimeric PVX bearing on its surface the 2F5 peptide (ELDKWAS (SEQ ID NO:4)) derived from the coat protein gp41 of the HIV-1 virus was produced in the ENEA laboratory for the production of a vaccine (Marusic et al. 2001 and patent application RM2000A000327).

During the subsequent cloning of other peptides of immunological interest, a spontaneous mutant deriving from one of these new chimeras was identified in vivo. The virus had rearranged itself in such a way as to eliminate the additional heterologous sequence, which evidently destabilized it. During this process, however, it also lost a region consisting of the 5' portion of the CP gene, corresponding to the 63 nucleotides coding for the first 21 aa of the CP, and its subgenomic promoter (FIG. 4*b*). The nucleotide rearrangement is such as to re-establish the ATG of the CP. This appears evident from the nucleotide (FIG. 5) and protein (FIG. 6) alignment of the wild-type (wt) CP and mutant. Notwithstanding this major deletion, the mutant CP gave rise to a stable virus in subsequent generations, and it was thus hypothesized that the mutant (called PVX-CC) could be used for in-fusion cloning with much longer CP sequences than those supported by the wt CP. The sequence of this mutant was therefore stably cloned in the pPVX201 vector, as a replacement for the wt CP, giving rise to the pPVX-CC plasmid. In this operation, the NheI site useful for cloning also came to be eliminated, so the pPVX-CC plasmid was further modified to facilitate subsequent cloning by inserting the single SmaI/XmaI restriction site, with a nucleotide sequence CCCGGG, corresponding to the amino acids proline and glycine (FIG. 4*c*). The nucleotide and protein sequence of the new CP, which originates a virus called PVX-Sma (Lico et al. 2006), was thus further modified compared to CP-CC, as is evident from the nucleotide (FIG. 7) and protein (FIG. 6) alignment. The new mutant is stable in subsequent generations and shows normal fitness and symptoms in vivo.

From the viewpoint of its application, the use of the mutant for cloning a broad-spectrum antimicrobial peptide (Donini et al. 2005) and a peptide deriving from the influenza virus for a new vaccine formulation (Lico et al. 2009) is known.

According to the present invention, the pPVX-Sma plasmid was used to insert, at the 5' end of the CP-Sma gene, the sequence coding for the LIP peptide. The plasmid thus obtained was then used to produce chimeric viral particles of PVX which expose, as the capsid protein, the fusion protein containing the capsid protein-Sma and LIP peptide.

It was found that the chimeric virus particle of PVX according to the present invention can be advantageously used for the in vitro diagnosis of SS, in particular using the ELISA method.

A comparison between the results of the ELISA using the synthetic peptide and the peptide mounted on the PVX viral scaffold showed a sensitivity, i.e. the ability to identify patients affected by the disease, of 84.7% and 97.1%, respectively; whereas the specificity, i.e. the ability to correctly identify healthy subjects is equal to 90.0% in both systems.

The analysis conducted on a subgroup of patients with SS who were characterized by an ANA-negative antibody profile and recognized as having the disease based on the presence of histopathological evidence drawn from the salivary gland biopsy used to diagnose the disease was of particular interest. In these patients the ELISA test performed with the chimeric viral particles according to the present invention demonstrated a greater sensitivity than the same ELISA test with the synthetic peptide, i.e. 98.7% versus 75%. The data for ANA-negative subjects is of particular interest, since in this subgroup of patients the evidence of a positive test for this new autoantigen would make it possible to avoid relying on a salivary gland biopsy in order to achieve diagnostic certainty, with considerable savings in terms of both costs and times (time for scheduling the biopsy and subsequent wait for the histological test), as well as reduced patient discomfort.

The subject matter of the present invention thus specifically relates to a fusion protein comprising or consisting of:

an amino-terminal portion consisting of a peptide sequence comprising or consisting of an antigenic determinant of lipocalin; and a carboxy-terminal portion consisting of a peptide sequence comprising or consisting of the capsid protein of a PVX virus, said capsid protein being intact or deleted in the 5' portion of the gene encodes the wild-type capsid protein, said amino-terminal portion being fused to said carboxy-terminal portion in such a way that said antigenic determinant is in frame with said capsid protein.

According to the present invention, said antigenic determinant of lipocalin can be selected in the group which consists of FEKAAGARGLST (SEQ ID NO:2), MSFEKAAGARGLST (SEQ ID NO:5).

The PVX virus whose capsid protein is used can be selected in the group consisting of PVX X3, BS, EX, NL4, HB, WS2, ROTH1, XS, UK3, OS, NL1, Taiwan, X4, preferably X3.

According to a particular embodiment of the present invention, the capsid protein used in the fusion protein according to the present invention consists of the following sequence:

(SEQ ID NO: 6)

```
PGTPATASGLFTIPDGDFFSTARAIVASNAVATNEDLSKIEAIWKDMKVP

TDTMAQAAWDLVRHCADVGSSAQTEMIDTGPYSNGISRARLAAAIKEVCT

LRQFCMKYAPNVVWNWMLTNNSPPANWQAQGFKPEHKFAAFDFFNGVT

NPAAIMPKEGLIRPPSEAEMNAAQTAAFVKITKARAQSNDFASLDAAVIR

GRITGTTTAEAVVTLPPP.
```

This protein is obtained by deletion in the 5' portion of the CP gene corresponding to the nucleotides 1-63 coding for aa 1-21 of the CP.

In particular, the fusion protein according to the present invention can have the following sequence:

(SEQ ID NO: 7)

```
MSFEKAAGARGLSTPGTPATASGLFTIPDGDFFSTARAIVASNAVATNED

LSKIEAIWKDMKVPTDTMAQAAWDLVRHCADVGSSAQTEMIDTGPYSN

GISRARLAAAIKEVCTLRQFCMKYAPVVVVNWMLTNNSPPANWQAQGFK

PEHKFAAFDFFNGVINPAAIMPKEGLIRPPSEAEMNAAQTAAFVKITKAR

AQSNDFASLDAAVTRGRITGTTTAEAVVTLPPP
```

The present invention further relates to a polynucleotide which codes for the fusion protein as defined above. In particular, the polynucleotide can have the following sequence (SEQ ID NO:8):

```
atgtcttttgaaaaggctgctggtgctagaggtttgtctactcccgggac

tcctgccacagcttcaggcctgttcaccatcccggatggggatttcttta

gtacagcccgtgccatagtagccagcaatgctgtcgcaacaaatgaggac

ctcagcaagattgaggctatttggaaggacatgaaggtgcccacagacac

tatggcacaggctgcttgggacttagtcagacactgtgctgatgtaggat

catccgctcaaacagaaatgatagatacaggtccctattccaacggcatc

agcagagctagactggcagcagcaattaaagaggtgtgcacacttaggca

attttgcatgaagtatgctccagtggtatggaactggatgttaactaaca

acagtccacctgctaactggcaagcacaaggtttcaagcctgagcacaaa

ttcgctgcattcgacttcttcaatggagtcaccaacccagctgccatcat

gcccaaagaggggctcatccggccaccgtctgaagctgaaatgaatgctg

cccaaactgctgcctttgtgaagattacaaaggccagggcacaatccaac

gactttgccagcctagatgcagctgtcactcgaggtcgtatcactggaac

aacaaccgctgaggctgttgtcactctaccaccaccataa
```

The subject matter of the present invention is further represented by an expression vector comprising the polynucleotide as defined above. Moreover, the present invention relates to a host cell comprising the expression vector as defined above.

According to a further embodiment, the present invention relates to a genome sequence of a PVX virus, said genome sequence comprising the polynucleotide as defined above.

Moreover, the present invention relates to a chimeric virus particle of potato virus X, said chimeric virus particle being characterized in that it comprises, as a capsid protein, the fusion protein of the present invention as defined above, said viral particle having exposed, on the outside thereof, the amino-terminal portion comprising or consisting of an antigenic determinant of lipocalin.

The viral genome contained in the chimeric virus particle consists of the genome sequence as defined above.

The present invention further relates to the use of the chimeric virus particle according to the present invention, or of the fusion protein as defined above, for the in vitro diagnosis of Sjögren's Syndrome, for example using the ELISA, dipstick or microchip method.

Therefore, the subject matter of the present invention further relates to a kit for the diagnosis in vitro of Sjögren's Syndrome, said kit comprising or consisting of the chimeric virus particle as defined above, or in the fusion protein as defined above, possibly in combination with suitable reagents for detection purposes. For example, the kit can be a kit ELISA, dipstick or microchip.

The present invention relates to moreover a plant, preferably belonging to the family of the Solanaceae, including *Solanum lycopersicon, Solanum tuberosum*, and the plants belonging to the genus *Nicotiana*, and in particular *N. benthamiana*, said plant being characterized in that it comprises within it the viral chimeric particle as defined above, or the expression vector as defined above.

The present invention also relates to plant cells of the plant as defined above and which express the chimeric viral particle as defined above, or the expression vector as defined above.

The subject matter of the present invention further relates to the use of a peptide sequence comprising or consisting of an antigenic determinant of lipocalin for the preparation of the fusion protein as defined above, the chimeric viral particle as defined above, the plant as defined above, and of plant cells as defined above.

Moreover, the present invention relates to the use of the plant as defined above or of the plant cells as defined above, for the production of the chimeric viral particle as defined above.

The subject matter of the present invention further relates to a process for the preparation of the fusion protein according to the present invention, said process comprising or consisting of the following steps:

a) cloning, in a vector, the peptide sequence comprising or consisting in the capsid protein of a PVX virus, said capsid protein being intact or deleted in the 5' portion of the gene which encodes the wild-type capsid protein; and b) cloning a peptide sequence comprising or consisting in an antigenic determinant of lipocalin, said peptide sequence being fused to said peptide sequence comprising or consisting in the capsid protein of a PVX virus in the vector resulting from step a).

As mentioned above, said antigenic determinant of lipocalin can be selected in the group which consists of FEKAAGARGLST (SEQ ID NO:2), MSFEKAAGARGLST (SEQ ID NO:5).

The PVX virus that can be used according to the present invention can be selected in the group consisting of PVX X3, BS, EX, NL4, HB, WS2, ROTH1, XS, UK3, OS, NL1, Taiwan, X4, preferably X3.

According to a particular embodiment, said capsid protein can consist of the following sequence:

```
                                    (SEQ ID NO: 6)
MPGTPATASGLFTIPDGDFFSTARAIVASNAVATNEDLSKIEAIWKDMKV

PTDTMAQAAWDLVRHCADVGSSAQTEMIDTGPYSNGISRARLAAAIKEV

CTLRQFCMKYAPVVWNWMLTNNSPPANWQAQGFKPEHKFAAFDFFNG

VTNPAAIMPKEGLIRPPSEAEMNAAQTAAFVKITKARAQSNDFASLDAAV

TRGRITGTTTAEAVVTLPPP.
```

The protein is obtained by deletion in the 5' portion of the CP gene corresponding to nucleotides 1-63 coding for the aa 1-21 of the CP.

The present invention further relates to a process for the preparation of the chimeric viral particle according to the present invention, said process comprising or consisting of the step of replacing the capsid protein of a PVX virus, in said PVX virus, with the fusion protein defined above.

The process for the production of the viral particle according to the present invention can comprise or consist of the following steps:

a1) infecting a plant, preferably belonging to the family Solanaceae, including *Solanum lycopersicon, Solanum tuberosum*, and plants belonging to the genus *Nicotiana*, and in particular *N. benthamiana* and *N. tabacum*, with the viral particle as defined above or the expression vector as defined above;

b1) cultivating the plant obtained according to the step a1);

c) extracting said viral particle from said plant.

The present invention will now be described, by way of illustration and not by way of limitation, according to a preferred embodiment thereof, with particular reference to the figures of the appended drawings, in which:

FIG. 1 shows a diagram representation of the genome of the potato virus X; RdRp, RNA-dependent RNA polymerase; MT, methyltransferase domain; HEL, helicase domain; POL, polymerase domain; 25K/12K/8K, movement proteins; CP, capsid protein; SGP, subgenomic promoter; sgRNA, subgenomic RNA; 7-methylguanine cap; terminal cap 5'; Poly(A): 3' terminal poly(A) tail.

FIG. 2 shows a schematic representation of how the viral genome can be modified and how a chimeric virus particle (CVP) is constructed. A) modification by gene insertion: the nucleotide sequence encoding the protein of interest is added to the viral genome with a duplication of the subgenomic promoter of the CP. B) modification by gene fusion: the nucleotide sequence encoding the protein/peptide of interest is fused to the 5' portion of the CP gene (N-terminal portion of the protein).

R, viral replicase; M, movement proteins; CP, coat protein, capsid protein; arrow, viral subgenomic promoter.

FIG. 3 shows a schematic representation of the plasmid pPVX201 containing the genome of the PVX subform of cDNA, 35S, promoter derived from CaMV; 5'UTR: 5' untranslated region; RdRp, RNA-dependent viral replicase; p8/p12/p25, viral movement proteins; prom sg CP, subgenomic promoter of the CP; prom sg2CP, duplicate subgenomic promoter of the CP; CP, coat protein; 3'UTR: 3' untranslated region; NOS term, terminator derived from the nopaline synthase gene of *A. tumefaciens*; beta-lactamase: gene coding for the beta-lactamase. The main restriction sites and their corresponding nucleotide position on the vector are indicated.

FIG. 4 shows a schematic representation of the plasmid containing the PVX genome in the form of cDNA, both the wild-type and mutant variants with the deletion at 5' of the CP gene. The subsequent panels show the region undergoing modification in detail, with the main restriction sites, the two oligonucleotides (PVX Back and New) used in the PCR reactions and their respective nucleotide positions. A) pPVX201: the plasmid containing the wild genome of PVX (it originates wild-type viral particles, wt PVX). B) pPVXCC: the plasmid derived from pPVX201 containing the mutant with the N-terminal deletion of the CP. C) pPVX-Sma: the plasmid derived from pPVX-CC and further modified and used in this patent to construct the chimeric viral particles PVX-LIP.

FIG. 5 shows the nucleotide alignment between the CP gene of wt PVX (SEQ ID NO: 16) and that of the deleted CP of PVX-CC (SEQ ID NO: 15).

FIG. 6 shows the protein alignment between the CP of wt PVX (SEQ ID NO: 17), that of the deleted one of PVX-CC (SEQ ID NO: 18) and the deleted and mutated one of PVX-Sma (SEQ ID NO: 19).

FIG. 7 shows the nucleotide alignment between the deleted CP gene of PVX-CC (SEQ ID NO: 15) and that of the deleted and mutated CP of PVX-Sma (SEQ ID NO: 20).

EXAMPLE 1: PREPARATION OF THE CHIMERIC VIRAL PARTICLE PVX ACCORDING TO THE PRESENT INVENTION

Preparation of PVX.LIP

The pPVX-Sma plasmid was purified on a small scale and digested with the restriction enzymes NheI and XmaI to insert the sequence coding for the LIP peptide at the 5' end of the CP-Sma gene.

This sequence was obtained by in vitro pairing of two complementary synthetic oligonucleotides carrying suitable hemi-restriction sites at their ends, to enable cloning directly in the receiving viral vector, duly digested.

The protocol provides for the dilution in water of equimolar amounts of the two strands (sense and antisense) and boiling of the solution for 5 minutes; after cooling at room temperature the complementary strands will pair.

The designed oligonucleotides are the following:

```
sense LIP:
                                    (SEQ ID NO: 9)
5'-CTAGC CTCGAG ATG TCT TTT GAA AAG GCT GCT
GGT GCT AGA GGT TTG TCT ACT C-3'

antisense LIP:
                                    (SEQ ID NO: 10)
5'-CCGGG AGT AGA CAA ACC TCT AGC ACC AGC
AGC CTT TTC AAA AGA CAT CTCGAG G-3'
```

Figure 1:
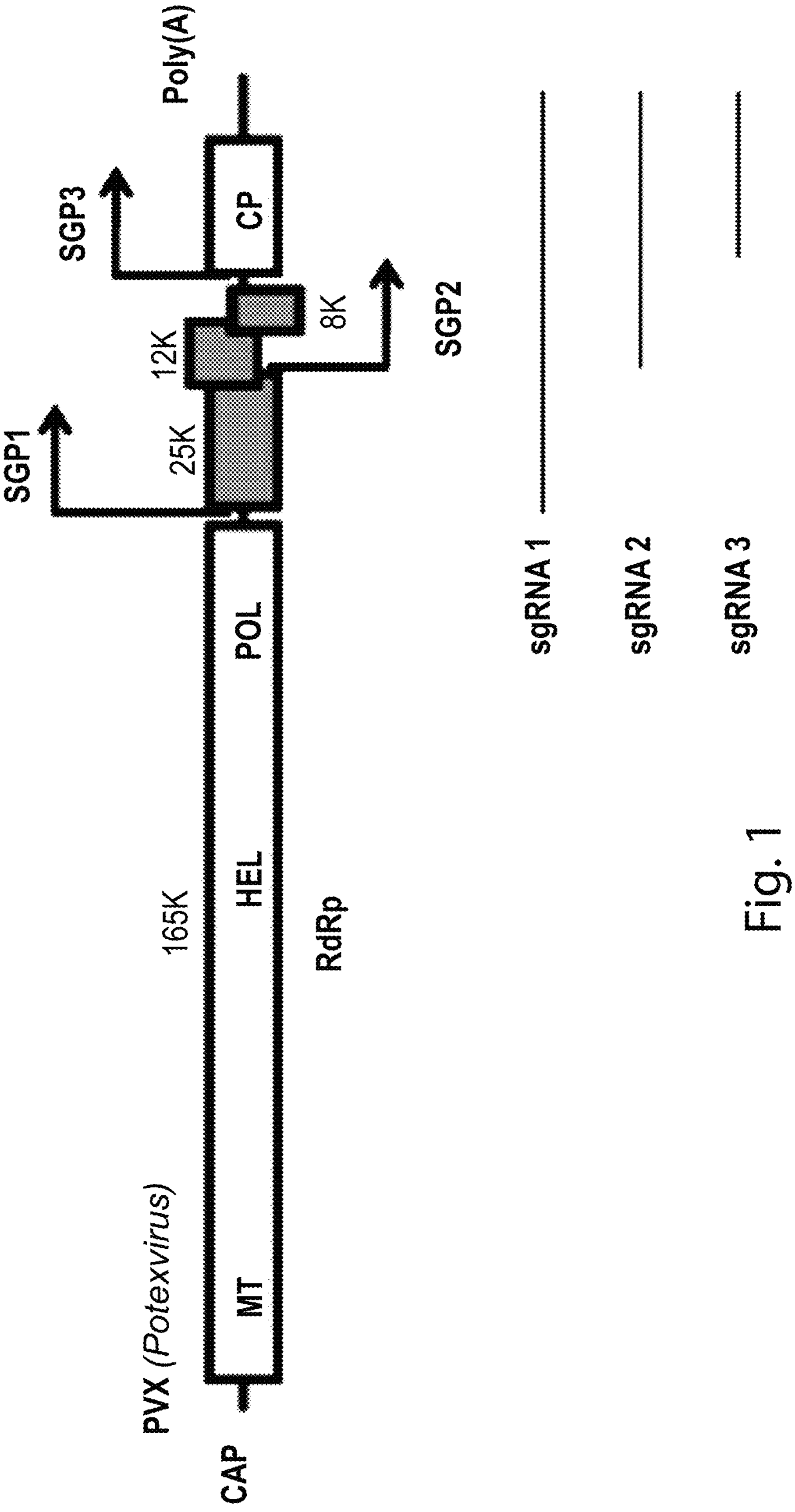
Figure 2:
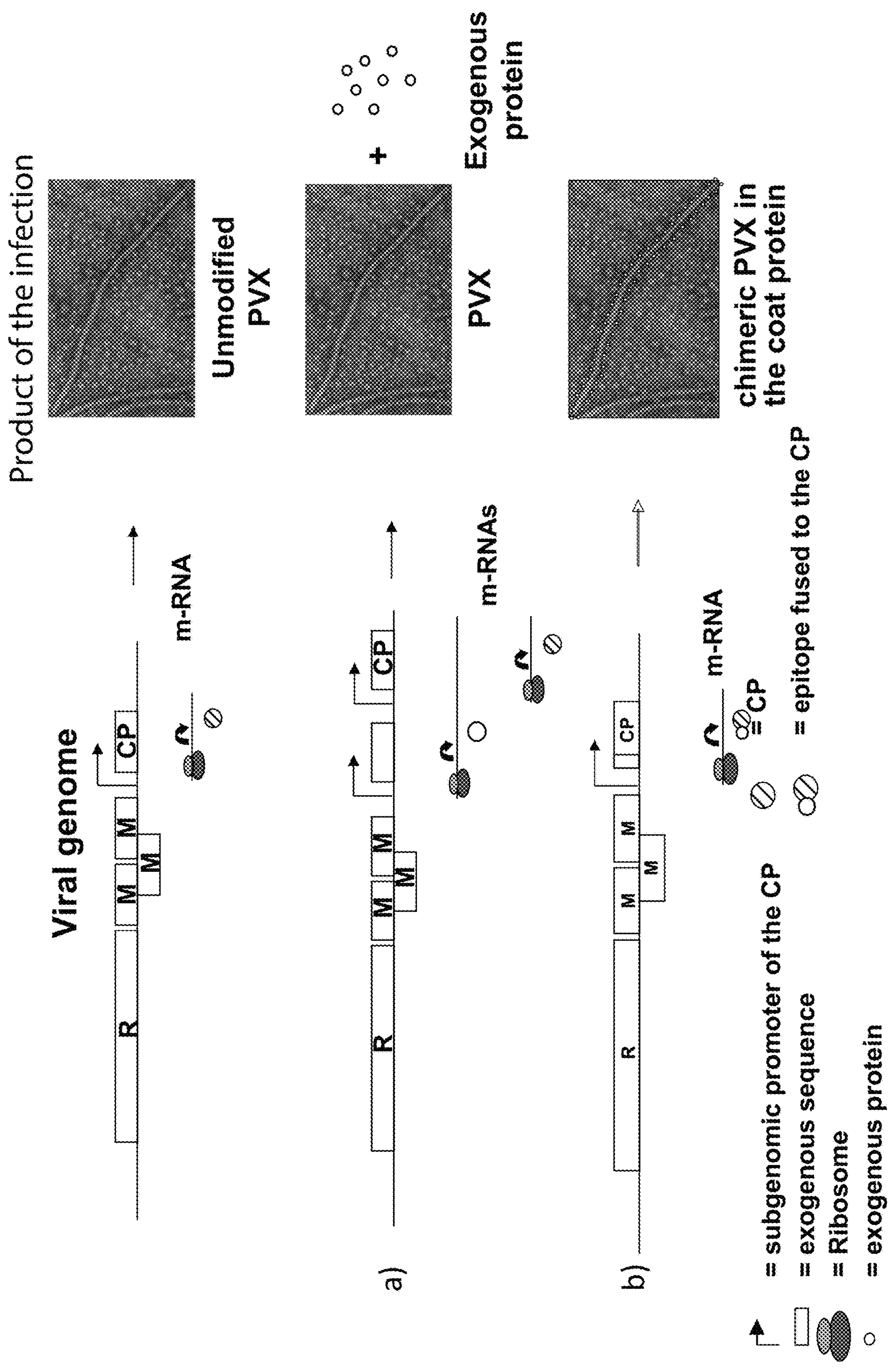
Figure 3:
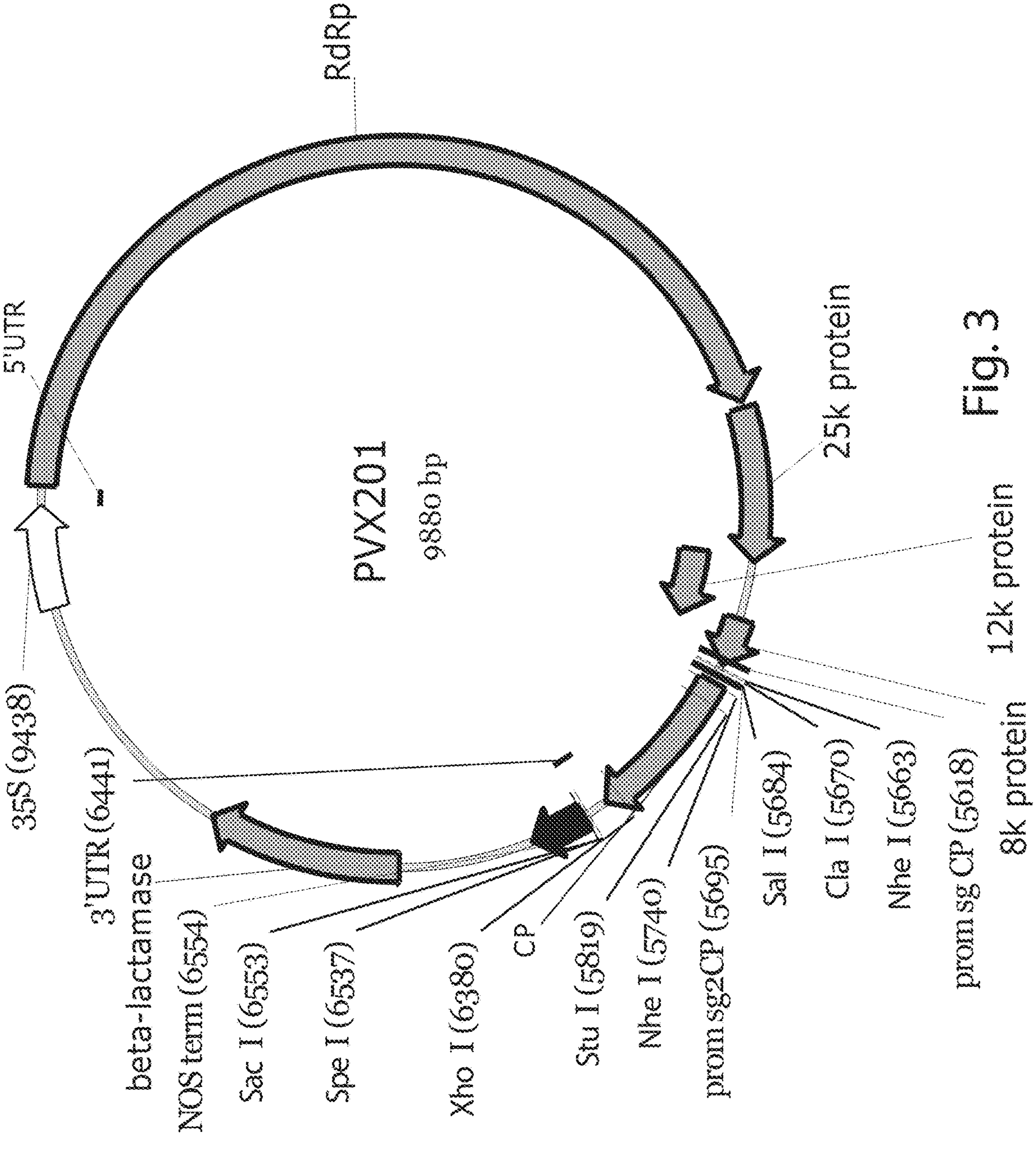
Figure 4:
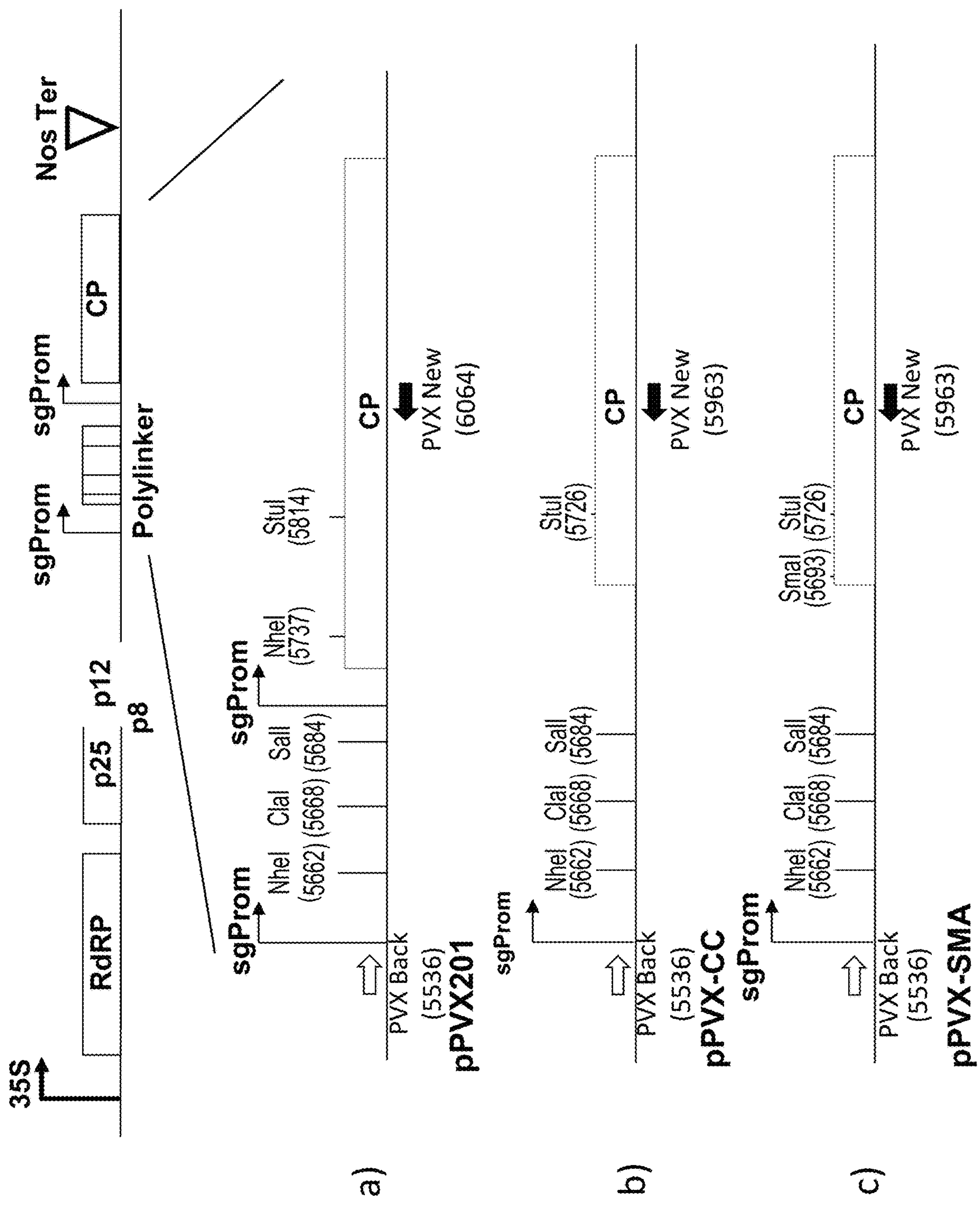

The sense and antisense oligonucleotides coding for the LIP peptide were designed in such a way as to have the codon usage of *Nicotiana benthamiana*, the 5' end compatible with the NheI restriction hemisite and the 3' end compatible with the XmaI hemisite, so that once in vitro pairing had taken place they would be ready for direct cloning in the pPVX-Sma plasmid digested with NheI-XmaI (FIG. 4*c*). Moreover, a serine was inserted immediately after the initial methionine to improve the characteristics of stability of the chimera in vivo.

The doubly digested pPVX-Sma plasmid was purified from the agarose gel using a commercial kit and the quantity and quality were re-verified in agarose gel and by spectrophotometric analysis.

On completion of the ligation reaction between the digested and purified vector and the oligonucleotides paired in vitro, the recombinant plasmid obtained is inserted into bacterial cells of the XL1-Blue strain by electroporation and plated in selective LB-agar medium containing ampicillin. The plates are incubated at 37° C. and the resulting colonies analysed by PCR with oligonucleotides specific for the nucleotide region of the PVX vector straddling the cloned region (FIG. 4):

```
5' back
                                (SEQ ID NO: 11)
5' AGCAGTCATTAGCACTTC 3'

3' new
                                (SEQ ID NO: 12)
5' CACCTTCATGTCCTTCCA 3'
```

The expected band is 370 bases. The positive colonies were used for small-scale purification of the plasmid and analysis thereof via sequencing in order to verify the correct presence of the additional LIP sequence. The positive clone identified was purified on a large scale and used for a first cycle of infections of plants of *N. benthamiama*. The plants of *N. benthamiana* were grown in hothouses with a photoperiod of 16 hours of light and 8 hours of darkness, at a constant temperature of 24° C. The light intensity in the hothouses is about 16000 lux.

For every leaf of *N. benthamiana* to be infected (2 leaves per plant) a solution containing 20 μg of plasmid diluted in 50 μl of water is prepared for the primary infection, whilst for the subsequent infections 50 μl of crude extract drawn from the infected tissue is used. The infection is carried out mechanically on the adaxial (upper) side of the leaf by lightly rubbing with the fingers in the presence both of the prepared solution and silicon carbide, or Carborundum (VWR International, Prolabo). The action of this powder causes microabrasions on the leaf surface, enabling the plasmid to enter effectively into the plant cells and express themselves.

After the onset of systemic symptoms in a time and manner similar to PVX-wt was verified, the tissue was used to:

1. extract the viral RNA, carry out a reverse transcription to DNA (RT) and a PCR, sequence the PCR fragment and verify the correct presence of the LIP sequence at the nucleotide level;

2. derive a crude protein extract with which to repeat a cycle of infection in vivo.

The entire process was then repeated another time to determine the stability of the chimeric PVX for LIP over three generations.

In order to determine the stability of the chimeric PVX, between 6 and 8 days after the infection, RNA was extracted from the systemically infected leaves by means of the RNeasy plant mini kit (Qiagen) (http://www1.qiagen.com/literature/render.aspx?id=352) and RT-PCR reactions were carried out using the GeneAmp RNA PCR Kit (Perkin Elmer). The cDNA was synthesized with oligo d(T) and PCR was performed using the 5' back and 3' new oligonucleotides. The cDNA thus obtained was sequenced and the presence of the correct sequence coding for the LIP peptide was verified.

Then followed a large-scale infection with purification of the chimeric PVX (PVX-LIP) and PVX devoid of the LIP peptide (PVX-wt) as a control.

For the purpose of protein extraction, the plant tissue, frozen at −80° C. and mechanically pulverized in a mortar chilled in liquid nitrogen, is mixed in an equivalent volume of phosphate-buffered saline 1× (1×PBS) (10 mM Na2HPO4, 10 mM NaH2PO4, 150 mM NaCl, pH 7.2) and mechanically crushed using an Ultraturrax electric homogenizer brought up to maximum speed. The homogenate must then be centrifuged at about 20000 g for 3 minutes.

For the purification of the chimeric viral particles, the following protocol is used.

Homogenize 50 g of tissue stored at −80° C. and pulverized with a mortar and pestle in 2 volumes of cold boric acid 0.5 M pH 7.8 (about 200-300 ml); filter the mixture through 3 layers of sterile gauze and adjust the pH to 6.5 with HCl. Then add 0.2% (w/v) of ascorbic acid and 0.2% (w/v) of sodium sulphite and leave under stirring until completely dissolved. Remove the particulate by centrifuging at 5500 g for 20 minutes at 4° C. and leave the supernatant a room temperature for 3 hours after having added 0.15 volumes of a 0.5% silver nitrate solution. After repeating the centrifugation at 5500 g for 20 minutes at 4° C., allow the supernatant to settle overnight at 4° C. in 0.2 volumes of a solution containing 1M NaCl and 20% PEG in boric acid 0.5 M pH 7.8. The next day, precipitate the viral particles by centrifuging at 8000 g for 30 minutes at 4° C., and resuspend the pellet in 10 ml of a solution containing boric acid 0.5 M, urea 0.5 M, 0.1% 2-mercaptoethanol, pH 7.8; centrifuge the mixture at 8000 g for 30 minutes at 4° C. Load the supernatant containing the virus on a 30% sucrose cushion prepared in water and centrifuge at 72500 g for 2 hours and 30 minutes at 4° C. Finally, resuspend the pellet in 1 ml of boric acid 0.5 M pH 7.8 and, after two hours of settling, centrifuge at 6000 g for 15 minutes at 4° C. The supernatant containing the virus is then loaded onto a 10-45% sucrose gradient prepared in boric acid and centrifuged at 90000 g for 1 hour. The individual fractions of the gradient are then analysed to identify those with the highest content of viral particles. The protocol is drawn from Udhe et al. 2005. The purified virus was dialyzed and concentrated by filtration through a membrane using Vivaspin 2 HS columns (Vivascience, http://teachline.ls.huji.ac.il/72682/Booklets/VIVASPIN_Ultrafiltration_products_II.pdf).

The purified virus was then analysed through silver-stained polyacrylamide gel to verify the degree of purity of the preparation and the presence of a band with a higher weight than the wt CP due to the presence of the LIP peptide and was quantified by reading with a spectrophotometer at a wavelength of 280 nm considering the molar extinction coefficient E equal to 1.25 ml/(mg*cm).

An LAL assay was also performed (following the protocol provided by pbi International); it verified the presence of endotoxins in the preparations described, presumably due to an "environmental" contamination given by the laboratory instrumentation. An EndoTrap red1/1 column (Hyglos) was used to remove the endotoxins, following the manufacturer's instructions.

The PVX-LIP and wt PVX viral particles were purified from the plant with a yield of 0.12 mg per gram of fresh tissue.

Preparation of CPMV.LIP

For the production of chimeric particles derived from the CPMV (Cowpea Mosaic Virus) which expose the LIP peptide, use was made of the pEAQ-HT system, in which the precursor of the coat protein (VP60) and the 24K protease are separately introduced in two pEAQ constructs to produce particles similar to empty viruses (devoid of genetic material). The sequence encoding the LIP peptide was cloned in the vector by ligation of the vector itself digested with the enzymes NheI and AatII and the sequence encoding the peptide obtained by pairing the primer CPMV—for 5'-CTAGC ACT CCT CCT GCT TTT GAA AAG GCT GCT GGT GCT AGA GGT TTG TCT ACT CCA TTT TCA GACGT-3' (SEQ ID NO:13) and the primer CPMV-rev 5'-C TGA AAA TGG AGT AGA CAA ACC TCT AGC ACC AGC AGC CTT TTC AAA AGC AGG AGG AGT G-3'(SEQ ID NO:14). The vector thus obtained, called pEAQ-HT-VP60-LIP, permits the exposure of the peptide in a BB-BC loop of the small subunit of the coat protein and in this manner the peptide is exposed on its outer surface. Subsequently, the vectors pEAQ-HT-VP60-LIP and pEAQ-HT-24K were electroporated in cells of *Agrobacterium tumefaciens* strain LBA4404 and both used to agroinfiltrate plants of *N. benthamiana*. In particular, the bacterial cultures transformed for the two vectors were made to grow separately in a liquid medium containing antibiotic agents, precipitated by centrifugation at 4000 g and resuspended in MMA (10 mM MES pH 5.6, 10 mM MgCl2 and 100 mM acetosyringone) until arriving at an O.D.600 equal to 0.8. Subsequently, after 4 h of incubation at room temperature, equal volumes of the two bacterial suspensions were mixed and used for infiltration, by means of a needleless syringe, of leaves of 4- to 5-week-old plants of *N. benthamiana*. Four leaves per plant were infiltrated. Samples were then taken of the infiltrated leaves 6 days after infiltration (dpi). For the expression of the empty CPMV the same procedure was carried out with the vectors pEAQ-HT-VP60 and pEAQ-HT-24K.

For the purification of the viral particles, 30 g of infiltrated leaves were processed. The plant material was homogenized with 4 volumes of sodium phosphate 0.1 M pH 7.0 containing 2% polyvinylpolypyrrolidone and a protease inhibitor (Complete EDTA-Free Cocktail, Roche, 04693132001).

The extract was clarified by filtration with two sheets of Miracloth paper (Merck Millipore, 475855-1R) and subsequent centrifugation (30000 g, 1 h, 4° C.). The supernatant was loaded onto an anion-exchange resin (DEAE Sephadex™ A-50, GE Healthcare, 17-0180-01), with a sample: resin ratio of 4:1. The flow-through was then concentrated at 4 ml, centrifuged (10000 g×10 minutes) and loaded into a size-exclusion chromatography column (HiPrep 16/60 Sephacryl S-500 HR, GE Healthcare, 28-9356-06) in 0.1 M sodium phosphate pH 7.0 containing 0.15 M of NaCl at a flow velocity of 0.8 ml/min. The eluted fractions were analysed using 12% SDS-PAGE gel stained with silver nitrate. The fractions containing CPMV. LIP and CPMV were joined separately and filtered with a 100 kDa centrifugal filter system (Amicon® Ultra-15, Merck Millipore, UFC910024). The purified particles were analysed using 12% SDS-PAGE gel stained with silver nitrate and subsequently quantified by reading the absorbance with a spectrophotometer at 280 nm.

EXAMPLE 2: ELISA DIAGNOSTIC TEST USING THE CHIMERIC VIRAL PARTICLE OF PVX ACCORDING TO THE PRESENT INVENTION

With the aim of optimizing the sensitivity and specificity of this diagnostic test and overcoming the methodological obstacles (type of plate), an assessment was made as to the advisability of performing an ELISA test that simultaneously exploited the synthetic LIP peptide and the LIP peptide expressed by chimeric particles of PVX (PVX-LIP), as well as by the control PVX, in order to be able to compare the result for the individual patient serum tested, by eliminating intra-experiment variability. We proceeded in an analogous manner, on a different plate, using the synthetic LIP peptide and the LIP peptide expressed by chimeric particles of CPMV, as well as by the control CPMV.

The following groups of subjects were enrolled in the present study:

1) 91 patients with the disease (5 men and 86 women) who met the AECG diagnostic criteria;
2) 60 healthy donors, comparable in terms of age and sex;
3) 60 patients with other autoimmune diseases (20 with systemic sclerosis, 20 with rheumatoid arthritis and 20 subjects with systemic lupus erythematosus).

In order to evaluate the bond of the antibodies present in the serum of the patients, ELISA assays (Immunolon II-Dynax and Maxisorp-NUNC) were set up with the LIP peptide produced by chemical synthesis and with PVX.LIP and wild-type CVP.

The plates were coated with 50 μl of 40 μg/ml of synthetic peptide in 1×PBS (2 micrograms of peptide) and with 50 μl of a 50 μg/ml solution of wild-type PVX and purified PVX.LIP (2.5 micrograms of chimeric CP corresponding to about 131.6 ng of peptide), similarly diluted in 1×PBS. The reference scale was obtained using known concentrations of immunoglobulin pools from donors (Sandoglobulin 50 and 100 μg/mL). The plates were then blocked using 3% BSA in 1×PBS and subsequently incubated with the serum of the subjects belonging to the three above-described experimental groups diluted 1:50 in 1×PBS with 1% BSA for 4 hours at room temperature. After the incubation, a sequence of washes was carried out, once with a solution of 1×PBS and Tween-20 and 3 successive washes in 1×PBS. Subsequently, the plates were incubated at 4° C. overnight with a human anti-IgG conjugated with alkaline phosphatase. At the end of the incubation the plates were treated with a new sequence of washes (1×PBS solution and Tween20 once and 3 successive washes in 1×PBS) and the signal was detected using p-nitrophenyl phosphate and a TECAN SUNRISE III microplate reader (wavelength 405 nm).

The result of the ELISA test revealed several difficulties of a methodological type. First, despite using plates polystyrene plates that were highly specific for the bond to small peptides, we had to limit the analysis of the result to plates that allowed the comparability of the data obtained, for the same subject, with the use of the synthetic LIP peptide and of the LIP peptide expressed by the chimeric particles of PVX and CPMV. Second, we had to discard the use of the LIP peptide expressed by the chimeric particles of CPMV, since the result obtained was not analysable. In fact, the absorbance obtained from the reaction with the viral particles alone, for all subjects, irrespective of whether they were patients or control subjects or affected by another autoimmune pathology, demonstrated to be higher than the value obtained with the LIP peptide expressed by the chimeric particles of CPMV. The CPMV system was thus excluded from the analysis and considered unsuitable for performing a diagnostic test.

The results of the ELISA test obtained using the synthetic peptide and the peptide mounted on the PVX viral scaffold showed a sensitivity of 84.7% and 97.1% respectively, whereas the specificity in both systems was equal to 90.0%.

The sensitivity of the ELISA test conducted using the peptide of the invention on the subgroup of patients with SS characterized by an ANA-negative antibody profile is equal to 98.7%, as compared to a value of 75% obtained with the use of the synthetic peptide.

In order to further validate the diagnostic method just described, we decided to assess the stability and reproducibility of the ELISA test with the PVX.LIP system. We therefore prepared plates coated with the PVX.LIP system (i.e. the wild-type PVX and PVX.LIP) and stored the same at 4° C. for use 1, 15, 30 and 60 days after coating them. The plates were tested with the serum of 30 subjects with SS, 10 patients with rheumatoid arthritis, 10 with Lupus and 10 control individuals and the result was substantially consistent. In particular, the data remained unchanged over time, both when we analysed the result for individual subjects or groups of subjects, and assessed the sensitivity and specificity of the test.

REFERENCES

Baulcombe D C, Chapman S, Santa Cruz S. (1995). Jellyfish green fluorescent protein as a reporter for virus infections. Plant J. 7: 1045-1053.

Bettelli E, Kom T, Oukka M, Kuchroo V K. (2008). Induction and effector functions of T(h)17 cells. Nature 453: 1051-1057.

Caffery B, Joyce E, Boone E, Slomovic A, Simpson T, Jones L, Senchyna M. (2008). Tear lipocalin and lysozyme in Sjogren and non-Sjogren dry eye. Optom Vis Sci 85: 661-667.

Cornec D, Saraux A, Cochener B, Pers J O, Jousse-Jolin S, Renaudineau Y, Marhadour T, Devauchelle-Pensec V. (2014) Level of agreement between 2002 American-European Consensus Group and 2012 American College of Rheumatology classification criteria for Sjögren's syndrome and reasons for discrepancies. Arthritis Res Ther. 16: R74.

Donini M, Lico C, Baschieri S, Conti S, Magliani W, Polonelli L, Benvenuto E. (2005). Production of an engineered killer peptide in *Nicotiana benthamiana* by using a Potato Virus X expression system. Appl Environ Microbiol. 71: 6360-6367.

Gachon A M, Lacazette E. (1998). Tear lipocalin and the eye's front line of defence. Br J Opthalmol. 82: 453-455.

Glasgow B J, Gasymov O K. (2011). Focus on molecules: tear lipocalin. Exp Eye Res. 92: 242-243.

Lee B H, Tudares M A, Nguyen C Q. (2009). Sjogren syndrome: an old tale with a new twist. Arch Immunol Ther Exp. 57: 57-66.

Lico C, Capuano F, Renzone G, Donini M, Marusic C, Scaloni A, Benvenuto E, Baschieri S. (2006). Peptide display on Potato virus X: molecular features of the coat protein-fused peptide affecting cell-to-cell and phloem movement of chimeric virus particles. J Gen Virol. 87: 3103-3112.

Lico C, Mancini C, Italiani P, Betti C, Boraschi D, Benvenuto E, Baschieri S. (2009). Plant-produced potato virus X chimeric particles displaying an influenza virus-derived peptide activate specific CD8+ T cells in mice. Vaccine 27: 5069-5076.

Marusic C, Rizza P, Lattanzi L, Mancini C, Spada M, Belardelli F, Benvenuto E, Capone I. (2001). Chimeric plant virus particles as immunogens for inducing murine and human immune responses against human immunodeficiency virus type 1. J Virol 75: 8434-8439.

Nardi N, Brito-Zeron P, Ramos-Casals M, Aguilo S, Cervera R, Ingelmo M et al. (2006). Circulating auto-antibodies against nuclear and non-nuclear antigens in primary Sjögren's syndrome: prevalence and clinical significance in 335 patients. Clin Rheumatol. 25: 341-346.

Navone R, Lunardi C, Gerli R, Tinazzi E, Peterlana D, Bason C, Corrocher R, Puccetti A. (2005). Identification of tear lipocalin as a novel autoantigen target in Sjögren's syndrome. J Autoimmun. 25: 229-234.

Qin Q, Wang H, Wang H Z, Huang Y L, Li H, Zhang W W, Zhang J R, He L L, Xia R, Zhao D B, Deng A M. (2014). Diagnostic accuracy of anti-alpha-fodrin antibodies for primary Sjögren's syndrome. Mod Rheumatol. 24:793-797.

Routsias J G, Tzioufas A G. (2007). Sjögren's syndrome-study of autoantigens and autoantibodies. Clin Rev Allergy Immunol. 32: 238-251.

Shiboski S C, Shiboski C H, Criswell L A, Baer A N, Challacombe S, Lanfranchi H, Schiødt M, Umehara H, Vivino F, Zhao Y, Dong Y, Greenspan D, Heidenreich A M, Helin P, Kirkham B, Kitagawa K, Larkin G, Li M, Lietman T, Lindergaard J, McNamara N, Sack K, Shirlaw P, Sugai S, Volleinweinder C, Whitcher J, Wu A, Zhang S, Zhang W, Greenspan J S. (2012). American College of rheumatology classification criteria for Sjögren's syndrome: a data-driven, expert consensus approach in the Sjögren's International Collaborative Clinical Alliance Cohort. Arthritis Care Res. 64: 475-487.

Uhde K, Fischer R, Commandeur U. (2005). Expression of multiple foreign epitopes presented as synthetic antigens on the surface of Potato virus X particles. Arch Virol. 150:327-340.

Vitali C, Bombardieri S, Jonsson R, Moutsopoulos H M, Alexander E L, Carsons S E, Daniels T E, FOX P C, Fox R I, Kassan S (2002). Classification criteria for Sjogren's syndrome: a revised version of the European criteria proposed by the American-European Consensus Group. Ann Rheum Dis. 61: 554-558.

The invention claimed is:

1. A method for in vitro diagnosis of Sjögren's Syndrome, the method comprising providing a chimeric virus particle; and ascertaining presence of autoantibodies against lipocalin;

wherein the chimeric virus particle comprises, as a capsid protein, a fusion protein comprising an amino-terminal portion consisting of a peptide sequence comprising an antigenic determinant of lipocalin and a carboxy-terminal portion consisting of a peptide sequence comprising a PVX virus capsid protein, wherein the PVX virus capsid protein is encoded by a wild-type capsid protein gene that is intact or deleted in the 5' portion of the gene, wherein the amino-terminal portion is fused to the carboxy-terminal portion such that the antigenic determinant is in frame with the capsid protein, and wherein the antigenic determinant is FEKAAGARGLST (SEQ ID NO:2) or MSFEKAAGARGLST (SEQ ID NO:5).

2. The method of claim 1, wherein ascertaining the presence of the autoantibodies comprises performing an ELISA, a dipstick, or a microchip method.

3. The method of claim 1, wherein said antigenic determinant is selected in the group which consists of FEKAAGARGLST (SEQ ID NO:2), MSFEKAAGARGLST (SEQ ID NO:5).

4. The method of claim 1, wherein the PVX virus is selected in the group consisting of PVX X3, BS, EX, NL4, HB, WS2, ROTH1, XS, UK3, OS, NL1, Taiwan, X4, preferably X3.

5. The method of claim 1, wherein said capsid protein consists of the following sequence:

(SEQ ID NO: 6)

PGTPATASGLFTIPDGDFFSTARAIVASNAVATNEDLSKIEAIWKDMKV

PTDTMAQAAWDLVRHCADVGSSAQTEMIDTGPYSNGISRARLAAAIKEV

CTLRQFCMKYAPVVWNWMLTNNSPPANWQAQGFKPEHKFAAFDFFNGVT

NPAAIMPKEGLIRPPSEAEMNAAQTAAFVKITKARAQSNDFASLDAAVT

RGRITGTTTAEAVVTLPPP.

6. The method of claim 1, said fusion protein having the following sequence:

(SEQ ID NO: 7)

MSFEKAAGARGLSTPGTPATASGLFTIPDGDFFSTARAIVASNAVATNE

DLSKIEAIWKDMKVPTDTMAQAAWDLVRHCADVGSSAQTEMIDTGPYSN

GISRARLAAAIKEVCTLRQFCMKYAPVVWNWMLTNNSPPANWQAQGFKP

EHKFAAFDFFNGVTNPAAIMPKEGLIRPPSEAEMNAAQTAAFVKITKAR

AQSNDFASLDAAVTRGRITGTTTAEAVVTLPPP.

* * * * *

SEQUENCE LISTING

```
<160> NUMBER OF SEQ ID NOS: 20

<210> SEQ ID NO 1
<211> LENGTH: 12
<212> TYPE: PRT
<213> ORGANISM: Artificial Sequence
<220> FEATURE:
<223> OTHER INFORMATION: Sjogren peptide

<400> SEQUENCE: 1

Gly Asp Arg Asp Ala Gly Ser Arg Gly Leu Val Ser
1               5                   10
```

<210> SEQ ID NO 2
<211> LENGTH: 12
<212> TYPE: PRT
<213> ORGANISM: Artificial Sequence
<220> FEATURE:
<223> OTHER INFORMATION: antigenic determinant of lipocalin

<400> SEQUENCE: 2

Phe Glu Lys Ala Ala Gly Ala Arg Gly Leu Ser Thr
1 5 10

<210> SEQ ID NO 3
<211> LENGTH: 9880
<212> TYPE: DNA
<213> ORGANISM: Artificial Sequence
<220> FEATURE:
<223> OTHER INFORMATION: sequence of pPVX201 plasmid

<400> SEQUENCE: 3
gaaaactaaa ccatacacca ccaacacaac caaacccacc acgcccaatt gttacacacc 60
cgcttgaaaa agaaagttta acaaatggcc aaggtgcgcg aggtttacca atcttttaca 120
gactccacca caaaaactct catccaagat gaggcttata gaaacattcg ccccatcatg 180
gaaaaacaca aactagctaa cccttacgct caaacggttg aagcggctaa tgatctagag 240
gggttcggca tagccaccaa tccctatagc attgaattgc atacacatgc agccgctaag 300
accatagaga ataaacttct agaggtgctt ggttccatcc taccacaaga acctgttaca 360
tttatgtttc ttaaacccag aaagctaaac tacatgagaa gaaacccgcg gatcaaggac 420
attttccaaa atgttgccat tgaaccaaga gacgtagcca ggtaccccaa ggaaacaata 480
attgacaaac tcacagagat cacaacggaa acagcataca ttagtgacac tctgcacttc 540
ttggatccga gctacatagt ggagacattc caaaactgcc caaaattgca aacattgtat 600
gcgaccttag ttctccccgt tgaggcagcc tttaaaatgg aaagcactca cccgaacata 660
tacagcctca aatacttcgg agatggtttc cagtatatac caggcaacca tggtggcggg 720
gcataccatc atgaattcgc tcatctacaa tggctcaaag tgggaaagat caagtggagg 780
gaccccaagg atagctttct cggacatctc aattacacga ctgagcaggt tgagatgcac 840
acagtgacag tacagttgca ggaatcgttc gcggcaaacc acttgtactg catcaggaga 900
ggagacttgc tcacaccgga ggtgcgcact ttcggccaac ctgacaggta cgtgattcca 960
ccacagatct tcctcccaaa agttcacaac tgcaagaagc cgattctcaa gaaaactatg 1020
atgcagctct tcttgtatgt taggacagtc aaggtcgcaa aaaattgtga catttttgcc 1080
aaagtcagac aattaattaa atcatctgac ttggacaaat actctgctgt ggaactggtt 1140
tacttagtaa gctacatgga gttccttgcc gatttacaag ctaccacctg cttctcagac 1200
acactttctg gtggcttgct aacaaagacc cttgcaccgg tgagggcttg gatacaagag 1260
aaaaagatgc agctgtttgg tcttgaggac tacgcgaagt tagtcaaagc agttgatttc 1320
cacccggtgg atttttcttt caaagtggaa acttgggact tcagattcca ccccttgcaa 1380
gcgtggaaag ccttccgacc aagggaagtg tcggatgtag aggaaatgga aagtttgttc 1440
tcagatgggg acctgcttga ttgcttcaca agaatgccag cttatgcggt aaacgcagag 1500
gaagatttag ctgcaatcag gaaaacgccc gagatggatg tcggtcaaga agttaaagag 1560
cctgcaggag acagaaatca atactcaaac cctgcagaaa ctttcctcaa caagctccac 1620
aggaaacaca gtagggaggt gaaacaccag gccgcaaaga aagctaaacg cctagctgaa 1680

-continued

```
atccaggagt caatgagagc tgaaggtgat gccgaaccaa atgaaataag cgggacgatg   1740
ggggcaatac ccagcaacgc cgaacttcct ggcacgaatg atgccagaca agaactcaca   1800
ctcccaacca ctaaacctgt ccctgcaagg tgggaagatg cttcattcac agattctagt   1860
gtggaagagg agcaggttaa actccttgga aaagaaaccg ttgaaacagc gacgcaacaa   1920
gtcatcgaag gacttccttg gaaacactgg attcctcaat taaatgctgt tggattcaag   1980
gcgctggaaa ttcagaggga taggagtgga acaatgatca tgcccatcac agaaatggtc   2040
tccgggctgg aaaaagagga cttccctgaa ggaactccaa aagagttggc acgagaattg   2100
ttcgctatga acagaagccc tgccaccatc cctttggacc tgcttagagc cagagactac   2160
ggcagtgatg taaagaacaa gagaattggt gccatcacaa agacacaggc aacgagttgg   2220
ggcgaatact tgacaggaaa gatagaaagc ttaactgaga ggaaagttgc gacttgtgtc   2280
attcatggag ctggaggttc tggaaaaagt catgccatcc agaaggcatt gagagaaatt   2340
ggcaagggct cggacatcac tgtagtcctg ccgaccaatg aactgcggct agattggagt   2400
aagaaagtgc ctaacactga gccctatatg ttcaagacct ctgaaaaggc gttaattggg   2460
ggaacaggca gcatagtcat ctttgacgat tactcaaaac ttcctcccgg ttacatagaa   2520
gccttagtct gtttctactc taaaatcaag ctaatcattc taacaggaga tagcagacaa   2580
agcgtctacc atgaaactgc tgaggacgcc tccatcaggc atttgggacc agcaacagag   2640
tacttctcaa aatactgccg atactatctc aatgccacac accgcaacaa gaaagatctt   2700
gcgaacatgc ttggtgtcta cagtgagaga acgggagtca ccgaaatcag catgagcgcc   2760
gagttcttag aaggaatccc aactttggta ccctcggatg agaagagaaa gctgtacatg   2820
ggcaccggga ggaatgacac gttcacatac gctggatgcc aggggctaac taagccgaag   2880
gtacaaatag tgttggacca caacacccaa gtgtgtagcg cgaatgtgat gtacacggca   2940
ctttctagag ccaccgatag gattcacttc gtgaacacaa gtgcaaattc ctctgccttc   3000
tgggaaaagt tggacagcac cccttacctc aagactttcc tatcagtggt gagagaacaa   3060
gcactcaggg agtacgagcc ggcagaggca gagccaattc aagagcctga gccccagaca   3120
cacatgtgtg tcgagaatga ggagtccgtg ctagaagagt acaaagagga actcttggaa   3180
aagtttgaca gagagatcca ctctgaatcc catggtcatt caaactgtgt ccaaactgaa   3240
gacacaacca ttcagttgtt ttcgcatcaa caagcaaaag atgagaccct cctctgggcg   3300
actatagatg cgcggctcaa gaccagcaat caagaaacaa acttccgaga attcctgagc   3360
aagaaggaca ttggggacgt tctgttttta aactaccaaa aagctatggg tttacccaaa   3420
gagcgtattc ctttttccca agaggtctgg gaagcttgtg cccacgaagt acaaagcaag   3480
tacctcagca agtcaaagtg caacttgatc aatgggactg tgagacagag cccagacttc   3540
gatgaaaata agattatggt attcctcaag tcgcagtggg tcacaaaggt ggaaaaacta   3600
ggtctaccca agattaagcc aggtcaaacc atagcagcct tttaccagca gactgtgatg   3660
ctttttggaa ctatggctag gtacatgcga tggttcagac aggctttcca gccaaaagaa   3720
gtcttcataa actgtgagac cacgccagat gacatgtctg catgggcctt gaacaactgg   3780
aatttcagca gacctagctt ggctaatgac tacacagctt tcgaccagtc tcaggatgga   3840
gccatgttgc aatttgaggt gctcaaagcc aaacaccact gcataccaga ggaaatcatt   3900
caggcataca tagatattaa gactaatgca cagattttcc taggcacgtt atcaattatg   3960
cgcctgactg gtgaaggtcc cacttttgat gcaaacactg agtgcaacat agcttacacc   4020
```

-continued

```
catacaaagt ttgacatccc agccggaact gctcaagttt atgcaggaga cgactccgca   4080
ctggactgtg ttccagaagt gaagcatagt ttccacaggc ttgaggacaa attactccta   4140
aagtcaaagc ctgtaatcac gcagcaaaag aagggcagtt ggcctgagtt ttgtggttgg   4200
ctgatcacac caaaaggggt gatgaaagac ccaattaagc tccatgttag cttaaaattg   4260
gctgaagcta agggtgaact caagaaatgt caagattcct atgaaattga tctgagttat   4320
gcctatgacc acaaggactc tctgcatgac ttgttcgatg agaaacagtg tcaggcacac   4380
acactcactt gcagaacact aatcaagtca gggagaggca ctgtctcact ttcccgcctc   4440
agaaactttc tttaaccgtt aagttacctt agagatttga ataagatgga tattctcatc   4500
agtagtttga aaagtttagg ttattctagg acttccaaat ctttagattc aggacctttg   4560
gtagtacatg cagtagccgg agccggtaag tccacagccc taaggaagtt gatcctcaga   4620
cacccaacat tcaccgtgca tacactcggt gtccctgaca aggtgagtat cagaactaga   4680
ggcatacaga agccaggacc tattcctgag ggcaacttcg caatcctcga tgagtatact   4740
ttggacaaca ccacaaggaa ctctaaccag gcactttttg ctgaccctta tcaggcaccg   4800
gagtttagcc tagagcccca cttctacttg gaaacatcat ttcgagttcc gaggaaagtg   4860
gcagatttga tagctggctg tggcttcgat ttcgagacca actcaccgga agaagggcac   4920
ttagagatca ctggcatatt caaagggccc ctactcggaa aggtgatagc cattgatgag   4980
gagtctgaga caacactgtc caggcatggt gttgagtttg ttaagccctg ccaagtgacg   5040
ggacttgagt tcaaagtagt cactattgtg tctgccgcac caatagagga aattggccag   5100
tccacagctt tctacaacgc tatcaccagg tcaaagggat tgacatatgt ccgcgcaggg   5160
ccataggctg accgctccgg tcaattctga aaaagtgtac atagtattag gtctatcatt   5220
tgctttagtt tcaattacct ttctgctttc tagaaatagc ttaccccacg tcggtgacaa   5280
cattcacagc ttgccacacg gaggagctta cagagacggc accaaagcaa tcttgtacaa   5340
ctccccaaat ctagggtcac gagtgagtct acacaacgga aagaacgcag catttgctgc   5400
cgttttgcta ctgactttgc tgatctatgg aagtaaatac atatctcaac gcaatcatac   5460
ttgtgcttgt ggtaacaatc atagcagtca ttagcacttc cttagtgagg actgaacctt   5520
gtgtcatcaa gattactggg gaatcaatca cagtgttggc ttgcaaacta gatgcagaaa   5580
ccataagggc cattgccgat ctcaagccac tctccgttga acggttaagt ttccattgat   5640
actcgaaaga ggtcagcacc agctagcatc gatcgcgata tcgtcgaccg ccgatgaacg   5700
gttaagtttc cattgatact cgaaagatgt cagcaccagc tagcacaaca cagcccatag   5760
ggtcaactac ctcaactacc acaaaaactg caggcgcaac tcctgccaca gcttcaggcc   5820
tgttcaccat cccggatggg gatttcttta gtacagcccg tgccatagta gccagcaatg   5880
ctgtcgcaac aaatgaggac ctcagcaaga ttgaggctat ttggaaggac atgaaggtgc   5940
ccacagacac tatggcacag gctgcttggg acttagtcag acactgtgct gatgtaggat   6000
catccgctca aacagaaatg atagatacag gtccctattc caacggcatc agcagagcta   6060
gactggcagc agcaattaaa gaggtgtgca cacttaggca attttgcatg aagtatgctc   6120
cagtggtatg gaactggatg ttaactaaca acagtccacc tgctaactgg caagcacaag   6180
gtttcaagcc tgagcacaaa ttcgctgcat tcgacttctt caatggagtc accaacccag   6240
ctgccatcat gcccaaagag gggctcatcc ggccaccgtc tgaagctgaa atgaatgctg   6300
cccaaactgc tgcctttgtg aagattacaa aggccagggc acaatccaac gactttgcca   6360
gcctagatgc agctgtcact cgaggtcgta tcactggaac aacaaccgct gaggctgttg   6420
```

```
tcactctacc accaccataa ctacgtctac ataaccgacg cctaccccag tttcatagta   6480
ttttctggtt tgattgtatg aataatataa ataaaaaaaa aaaaaaaaaa aaaaaactag   6540
tggtaccgag ctcgatcgtt caaacatttg gcaataaagt ttcttaagat tgaatcctgt   6600
tgccggtctt gcgatgatta tcatataatt tctgttgaat tacgttaagc atgtaataat   6660
taacatgtaa tgcatgacgt tatttatgag atgggttttt atgattagag tcccgcaatt   6720
atacatttaa tacgcgatag aaaacaaaat atagcgcgca aactaggata aattatcgcg   6780
cgcggtgtca tctatgttac tagatcgaat tcactggccg tcgttttaca acgtcgtgac   6840
tgggaaaacc ctggcgttac ccaacttaat cgccttgcag cacatccccc tttcgccagc   6900
tggcgtaata gcgaagaggc ccgcaccgat cgcccttccc aacagttgcg cagcctgaat   6960
ggcgaatggc gcctgatgcg gtattttctc cttacgcatc tgtgcggtat ttcacaccgc   7020
atatggtgca ctctcagtac aatctgctct gatgccgcat agttaagcca gccccgacac   7080
ccgccaacac ccgctgacgc gccctgacgg gcttgtctgc tcccggcatc cgcttacaga   7140
caagctgtga ccgtctccgg gagctgcatg tgtcagaggt tttcaccgtc atcaccgaaa   7200
cgcgcgagac gaaagggcct cgtgatacgc ctatttttat aggttaatgt catgataata   7260
atggtttctt agacgtcagg tggcactttt cggggaaatg tgcgcggaac ccctatttgt   7320
ttatttttct aaatacattc aaatatgtat ccgctcatga gacaataacc ctgataaatg   7380
cttcaataat attgaaaaag gaagagtatg agtattcaac atttccgtgt cgcccttatt   7440
ccctttttg cggcattttg ccttcctgtt tttgctcacc cagaaacgct ggtgaaagta   7500
aaagatgctg aagatcagtt gggtgcacga gtgggttaca tcgaactgga tctcaacagc   7560
ggtaagatcc ttgagagttt tcgccccgaa gaacgttttc caatgatgag cacttttaaa   7620
gttctgctat gtggcgcggt attatcccgt attgacgccg ggcaagagca actcggtcgc   7680
cgcatacact attctcagaa tgacttggtt gagtactcac cagtcacaga aaagcatctt   7740
acggatggca tgacagtaag agaattatgc agtgctgcca taaccatgag tgataacact   7800
gcggccaact tacttctgac aacgatcgga ggaccgaagg agctaaccgc ttttttgcac   7860
aacatggggg atcatgtaac tcgccttgat cgttgggaac cggagctgaa tgaagccata   7920
ccaaacgacg agcgtgacac cacgatgcct gtagcaatgg caacaacgtt gcgcaaacta   7980
ttaactggcg aactacttac tctagcttcc cggcaacaat taatagactg gatggaggcg   8040
gataaagttg caggaccact tctgcgctcg gcccttccgg ctggctggtt tattgctgat   8100
aaatctggag ccggtgagcg tgggtctcgc ggtatcattg cagcactggg gccagatggt   8160
aagccctccc gtatcgtagt tatctacacg acggggagtc aggcaactat ggatgaacga   8220
aatagacaga tcgctgagat aggtgcctca ctgattaagc attggtaact gtcagaccaa   8280
gtttactcat atatacttta gattgattta aaacttcatt tttaatttaa aaggatctag   8340
gtgaagatcc tttttgataa tctcatgacc aaaatccctt aacgtgagtt ttcgttccac   8400
tgagcgtcag accccgtaga aaagatcaaa ggatcttctt gagatccttt ttttctgcgc   8460
gtaatctgct gcttgcaaac aaaaaaacca ccgctaccag cggtggtttg tttgccggat   8520
caagagctac caactctttt tccgaaggta actggcttca gcagagcgca gataccaaat   8580
actgtccttc tagtgtagcc gtagttaggc caccacttca agaactctgt agcaccgcct   8640
acatacctcg ctctgctaat cctgttacca gtggctgctg ccagtggcga taagtcgtgt   8700
cttaccgggt tggactcaag acgatagtta ccggataagg cgcagcggtc gggctgaacg   8760
```

-continued

```
gggggttcgt gcacacagcc cagcttggag cgaacgacct acaccgaact gagataccta   8820

cagcgtgagc attgagaaag cgccacgctt cccgaaggga gaaaggcgga caggtatccg   8880

gtaagcggca gggtcggaac aggagagcgc acgagggagc ttccaggggg aaacgcctgg   8940

tatctttata gtcctgtcgg gtttcgccac ctctgacttg agcgtcgatt tttgtgatgc   9000

tcgtcagggg ggcggagcct atggaaaaac gccagcaacg cggccttttt acggttcctg   9060

gccttttgct ggccttttgc tcacatgttc tttcctgcgt tatcccctga ttctgtggat   9120

aaccgtatta ccgcctttga gtgagctgat accgctcgcc gcagccgaac gaccgagcgc   9180

agcgagtcag tgagcgagga agcggaagag cgcccaatac gcaaaccgcc tctccccgcg   9240

cgttggccga ttcattaatg cagctggcac gacaggtttc ccgactggaa agcgggcagt   9300

gagcgcaacg caattaatgt gagttagctc actcattagg caccccaggc tttacacttt   9360

atgcttccgg ctcgtatgtt gtgtggaatt gtgagcggat aacaatttca cacaggaaac   9420

agctatgacc atgattacgc caagcttgca tgcctgcagg tcaacatggt ggagcacgac   9480

acgcttgtct actccaaaaa tatcaaagat acagtctcag aagaccaaag ggcaattgag   9540

acttttcaac aaagggtaat atccggaaac ctcctcggat tccattgccc agctatctgt   9600

cactttattg tgaagatagt ggaaaaggaa ggtggctcct acaaatgcca tcattgcgat   9660

aaaggaaagg ccatcgttga agatgcctct gccgacagtg gtcccaaaga tggaccccca   9720

cccacgagga gcatcgtgga aaaagaagac gttccaacca cgtcttcaaa gcaagtggat   9780

tgatgtgata tctccactga cgtaagggat gacgcacaat cccactatcc ttcgcaagac   9840

ccttcctcta tataaggaag ttcatttcat ttggagagga                         9880
```

<210> SEQ ID NO 4
<211> LENGTH: 7
<212> TYPE: PRT
<213> ORGANISM: Artificial Sequence
<220> FEATURE:
<223> OTHER INFORMATION: HIV1 gp41 2F5 peptide

<400> SEQUENCE: 4

```
Glu Leu Asp Lys Trp Ala Ser
1               5
```

<210> SEQ ID NO 5
<211> LENGTH: 14
<212> TYPE: PRT
<213> ORGANISM: Artificial Sequence
<220> FEATURE:
<223> OTHER INFORMATION: antigenic determinant of lipocalin

<400> SEQUENCE: 5

```
Met Ser Phe Glu Lys Ala Ala Gly Ala Arg Gly Leu Ser Thr
1               5                   10
```

<210> SEQ ID NO 6
<211> LENGTH: 215
<212> TYPE: PRT
<213> ORGANISM: Artificial Sequence
<220> FEATURE:
<223> OTHER INFORMATION: PVX X3 capsid protein

<400> SEQUENCE: 6

```
Pro Gly Thr Pro Ala Thr Ala Ser Gly Leu Phe Thr Ile Pro Asp Gly
1               5                   10                  15

Asp Phe Phe Ser Thr Ala Arg Ala Ile Val Ala Ser Asn Ala Val Ala
            20                  25                  30
```

Thr Asn Glu Asp Leu Ser Lys Ile Glu Ala Ile Trp Lys Asp Met Lys
35 40 45

Val Pro Thr Asp Thr Met Ala Gln Ala Ala Trp Asp Leu Val Arg His
50 55 60

Cys Ala Asp Val Gly Ser Ser Ala Gln Thr Glu Met Ile Asp Thr Gly
65 70 75 80

Pro Tyr Ser Asn Gly Ile Ser Arg Ala Arg Leu Ala Ala Ala Ile Lys
85 90 95

Glu Val Cys Thr Leu Arg Gln Phe Cys Met Lys Tyr Ala Pro Val Val
100 105 110

Trp Asn Trp Met Leu Thr Asn Asn Ser Pro Pro Ala Asn Trp Gln Ala
115 120 125

Gln Gly Phe Lys Pro Glu His Lys Phe Ala Ala Phe Asp Phe Phe Asn
130 135 140

Gly Val Thr Asn Pro Ala Ala Ile Met Pro Lys Glu Gly Leu Ile Arg
145 150 155 160

Pro Pro Ser Glu Ala Glu Met Asn Ala Ala Gln Thr Ala Ala Phe Val
165 170 175

Lys Ile Thr Lys Ala Arg Ala Gln Ser Asn Asp Phe Ala Ser Leu Asp
180 185 190

Ala Ala Val Thr Arg Gly Arg Ile Thr Gly Thr Thr Thr Ala Glu Ala
195 200 205

Val Val Thr Leu Pro Pro Pro
210 215

<210> SEQ ID NO 7
<211> LENGTH: 229
<212> TYPE: PRT
<213> ORGANISM: Artificial Sequence
<220> FEATURE:
<223> OTHER INFORMATION: fusion protein obtained by fusion of SEQ ID NO:5 and SEQ ID NO:6

<400> SEQUENCE: 7

Met Ser Phe Glu Lys Ala Ala Gly Ala Arg Gly Leu Ser Thr Pro Gly
1 5 10 15

Thr Pro Ala Thr Ala Ser Gly Leu Phe Thr Ile Pro Asp Gly Asp Phe
20 25 30

Phe Ser Thr Ala Arg Ala Ile Val Ala Ser Asn Ala Val Ala Thr Asn
35 40 45

Glu Asp Leu Ser Lys Ile Glu Ala Ile Trp Lys Asp Met Lys Val Pro
50 55 60

Thr Asp Thr Met Ala Gln Ala Ala Trp Asp Leu Val Arg His Cys Ala
65 70 75 80

Asp Val Gly Ser Ser Ala Gln Thr Glu Met Ile Asp Thr Gly Pro Tyr
85 90 95

Ser Asn Gly Ile Ser Arg Ala Arg Leu Ala Ala Ala Ile Lys Glu Val
100 105 110

Cys Thr Leu Arg Gln Phe Cys Met Lys Tyr Ala Pro Val Val Trp Asn
115 120 125

Trp Met Leu Thr Asn Asn Ser Pro Pro Ala Asn Trp Gln Ala Gln Gly
130 135 140

Phe Lys Pro Glu His Lys Phe Ala Ala Phe Asp Phe Phe Asn Gly Val
145 150 155 160

Thr Asn Pro Ala Ala Ile Met Pro Lys Glu Gly Leu Ile Arg Pro Pro

```
            165                 170                 175

Ser Glu Ala Glu Met Asn Ala Ala Gln Thr Ala Ala Phe Val Lys Ile
        180                 185                 190

Thr Lys Ala Arg Ala Gln Ser Asn Asp Phe Ala Ser Leu Asp Ala Ala
    195                 200                 205

Val Thr Arg Gly Arg Ile Thr Gly Thr Thr Thr Ala Glu Ala Val Val
    210                 215                 220

Thr Leu Pro Pro Pro
225


<210> SEQ ID NO 8
<211> LENGTH: 690
<212> TYPE: DNA
<213> ORGANISM: Artificial Sequence
<220> FEATURE:
<223> OTHER INFORMATION: polynucleotide sequence encoding SEQ ID NO:7

<400> SEQUENCE: 8

atgtcttttg aaaaggctgc tggtgctaga ggtttgtcta ctcccgggac tcctgccaca     60

gcttcaggcc tgttcaccat cccggatggg gatttcttta gtacagcccg tgccatagta    120

gccagcaatg ctgtcgcaac aaatgaggac ctcagcaaga ttgaggctat ttggaaggac    180

atgaaggtgc ccacagacac tatggcacag gctgcttggg acttagtcag acactgtgct    240

gatgtaggat catccgctca aacagaaatg atagatacag gtccctattc caacggcatc    300

agcagagcta gactggcagc agcaattaaa gaggtgtgca cacttaggca attttgcatg    360

aagtatgctc cagtggtatg gaactggatg ttaactaaca acagtccacc tgctaactgg    420

caagcacaag gtttcaagcc tgagcacaaa ttcgctgcat tcgacttctt caatggagtc    480

accaacccag ctgccatcat gcccaaagag gggctcatcc ggccaccgtc tgaagctgaa    540

atgaatgctg cccaaactgc tgcctttgtg aagattacaa aggccagggc acaatccaac    600

gactttgcca gcctagatgc agctgtcact cgaggtcgta tcactggaac aacaaccgct    660

gaggctgttg tcactctacc accaccataa                                     690


<210> SEQ ID NO 9
<211> LENGTH: 54
<212> TYPE: DNA
<213> ORGANISM: Artificial Sequence
<220> FEATURE:
<223> OTHER INFORMATION: lipocalin forward primer

<400> SEQUENCE: 9

ctagcctcga gatgtctttt gaaaaggctg ctggtgctag aggtttgtct actc           54


<210> SEQ ID NO 10
<211> LENGTH: 54
<212> TYPE: DNA
<213> ORGANISM: Artificial Sequence
<220> FEATURE:
<223> OTHER INFORMATION: lipocalin reverse primer

<400> SEQUENCE: 10

ccgggagtag acaaacctct agcaccagca gccttttcaa aagacatctc gagg           54


<210> SEQ ID NO 11
<211> LENGTH: 18
<212> TYPE: DNA
<213> ORGANISM: Artificial Sequence
<220> FEATURE:
<223> OTHER INFORMATION: PVX vector forward primer
```

<400> SEQUENCE: 11
agcagtcatt agcacttc 18

<210> SEQ ID NO 12
<211> LENGTH: 18
<212> TYPE: DNA
<213> ORGANISM: Artificial Sequence
<220> FEATURE:
<223> OTHER INFORMATION: PVX vector reverse primer

<400> SEQUENCE: 12
caccttcatg tccttcca 18

<210> SEQ ID NO 13
<211> LENGTH: 67
<212> TYPE: DNA
<213> ORGANISM: Artificial Sequence
<220> FEATURE:
<223> OTHER INFORMATION: CPMV forward primer

<400> SEQUENCE: 13
ctagcactcc tcctgctttt gaaaaggctg ctggtgctag aggtttgtct actccatttt 60
cagacgt 67

<210> SEQ ID NO 14
<211> LENGTH: 59
<212> TYPE: DNA
<213> ORGANISM: Artificial Sequence
<220> FEATURE:
<223> OTHER INFORMATION: CPMV reverse primer

<400> SEQUENCE: 14
ctgaaaatgg agtagacaaa cctctagcac cagcagcctt ttcaaaagca ggaggagtg 59

<210> SEQ ID NO 15
<211> LENGTH: 651
<212> TYPE: PRT
<213> ORGANISM: Artificial Sequence
<220> FEATURE:
<223> OTHER INFORMATION: nucleotide sequence encoding PVX deleted capsid protein

<400> SEQUENCE: 15

```
Ala Thr Gly Thr Gly Thr Gly Cys Cys Ala Cys Thr Cys Cys Thr Gly
1               5                   10                  15

Cys Cys Ala Cys Ala Gly Cys Thr Thr Cys Ala Gly Gly Cys Cys Thr
            20                  25                  30

Gly Thr Thr Cys Ala Cys Cys Ala Thr Cys Cys Cys Gly Gly Ala Thr
        35                  40                  45

Gly Gly Gly Gly Ala Thr Thr Thr Cys Thr Thr Thr Ala Gly Thr Ala
    50                  55                  60

Cys Ala Gly Cys Cys Cys Gly Thr Gly Cys Cys Ala Thr Ala Gly Thr
65                  70                  75                  80

Ala Gly Cys Cys Ala Gly Cys Ala Ala Thr Gly Cys Thr Gly Thr Cys
                85                  90                  95

Gly Cys Ala Ala Cys Ala Ala Ala Thr Gly Ala Gly Gly Ala Cys Cys
            100                 105                 110

Thr Cys Ala Gly Cys Ala Ala Gly Ala Thr Thr Gly Ala Gly Gly Cys
        115                 120                 125

Thr Ala Thr Thr Thr Gly Gly Ala Ala Gly Gly Ala Cys Ala Thr Gly
```

-continued

```
    130                 135                 140

Ala Ala Gly Gly Thr Gly Cys Cys Cys Ala Cys Ala Gly Ala Cys Ala
145                 150                 155                 160

Cys Thr Ala Thr Gly Gly Cys Ala Cys Ala Gly Gly Cys Thr Gly Cys
                165                 170                 175

Thr Thr Gly Gly Gly Ala Cys Thr Thr Ala Gly Thr Cys Ala Gly Ala
            180                 185                 190

Cys Ala Cys Thr Gly Thr Gly Cys Thr Gly Ala Thr Gly Thr Ala Gly
        195                 200                 205

Gly Ala Thr Cys Ala Thr Cys Cys Gly Cys Thr Cys Ala Ala Ala Cys
    210                 215                 220

Ala Gly Ala Ala Ala Thr Gly Ala Thr Ala Gly Ala Thr Ala Cys Ala
225                 230                 235                 240

Gly Gly Thr Cys Cys Cys Thr Ala Thr Thr Cys Cys Ala Ala Cys Gly
                245                 250                 255

Gly Cys Ala Thr Cys Ala Gly Cys Ala Gly Ala Gly Cys Thr Ala Gly
            260                 265                 270

Ala Cys Thr Gly Gly Cys Ala Gly Cys Ala Gly Cys Ala Ala Thr Thr
        275                 280                 285

Ala Ala Ala Gly Ala Gly Gly Thr Gly Thr Gly Cys Ala Cys Ala Cys
    290                 295                 300

Thr Thr Ala Gly Gly Cys Ala Ala Thr Thr Thr Thr Gly Cys Ala Thr
305                 310                 315                 320

Gly Ala Ala Gly Thr Ala Thr Gly Cys Thr Cys Cys Ala Gly Thr Gly
                325                 330                 335

Gly Thr Ala Thr Gly Gly Ala Ala Cys Thr Gly Gly Ala Thr Gly Thr
            340                 345                 350

Thr Ala Ala Cys Thr Ala Ala Cys Ala Ala Cys Ala Gly Thr Cys Cys
        355                 360                 365

Ala Cys Cys Thr Gly Cys Thr Ala Ala Cys Thr Gly Gly Cys Ala Ala
    370                 375                 380

Gly Cys Ala Cys Ala Ala Gly Gly Thr Thr Thr Cys Ala Ala Gly Cys
385                 390                 395                 400

Cys Thr Gly Ala Gly Cys Ala Cys Ala Ala Ala Thr Thr Cys Gly Cys
                405                 410                 415

Thr Gly Cys Ala Thr Thr Cys Gly Ala Cys Thr Thr Cys Thr Thr Cys
            420                 425                 430

Ala Ala Thr Gly Gly Ala Gly Thr Cys Ala Cys Cys Ala Ala Cys Cys
        435                 440                 445

Cys Ala Gly Cys Thr Gly Cys Cys Ala Thr Cys Ala Thr Gly Cys Cys
    450                 455                 460

Cys Ala Ala Ala Gly Ala Gly Gly Gly Gly Cys Thr Cys Ala Thr Cys
465                 470                 475                 480

Cys Gly Gly Cys Cys Ala Cys Cys Gly Thr Cys Thr Gly Ala Ala Gly
                485                 490                 495

Cys Thr Gly Ala Ala Ala Thr Gly Ala Ala Thr Gly Cys Thr Gly Cys
            500                 505                 510

Cys Cys Ala Ala Ala Cys Thr Gly Cys Thr Gly Cys Cys Thr Thr Thr
        515                 520                 525

Gly Thr Gly Ala Ala Gly Ala Thr Thr Ala Cys Ala Ala Ala Gly Gly
    530                 535                 540

Cys Cys Ala Gly Gly Gly Cys Ala Cys Ala Ala Thr Cys Cys Ala Ala
545                 550                 555                 560
```

```
Cys Gly Ala Cys Thr Thr Thr Gly Cys Cys Ala Gly Cys Cys Thr Ala
                565                 570                 575

Gly Ala Thr Gly Cys Ala Gly Cys Thr Gly Thr Cys Ala Cys Thr Cys
            580                 585                 590

Gly Ala Gly Gly Thr Cys Gly Thr Ala Thr Cys Ala Cys Thr Gly Gly
        595                 600                 605

Ala Ala Cys Ala Ala Cys Ala Ala Cys Cys Gly Cys Thr Gly Ala Gly
    610                 615                 620

Gly Cys Thr Gly Thr Thr Gly Thr Cys Ala Cys Thr Cys Thr Ala Cys
625                 630                 635                 640

Cys Ala Cys Cys Ala Cys Cys Ala Thr Ala Ala
                645                 650
```

<210> SEQ ID NO 16
<211> LENGTH: 714
<212> TYPE: DNA
<213> ORGANISM: Artificial Sequence
<220> FEATURE:
<223> OTHER INFORMATION: nucleotide sequence encoding PVX capsid protein

<400> SEQUENCE: 16

```
atgtcagcac cagctagcac aacacagccc atagggtcaa ctacctcaac taccacaaaa     60

actgcaggcg caactcctgc cacagcttca ggcctgttca ccatcccgga tggggatttc    120

tttagtacag cccgtgccat agtagccagc aatgctgtcg caacaaatga ggacctcagc    180

aagattgagg ctatttggaa ggacatgaag gtgcccacag acactatggc acaggctgct    240

tgggacttag tcagacactg tgctgatgta ggatcatccg ctcaaacaga aatgatagat    300

acaggtccct attccaacgg catcagcaga gctagactgg cagcagcaat taaagaggtg    360

tgcacactta ggcaattttg catgaagtat gctccagtgg tatggaactg gatgttaact    420

aacaacagtc cacctgctaa ctggcaagca caaggtttca agcctgagca caaattcgct    480

gcattcgact tcttcaatgg agtcaccaac ccagctgcca tcatgcccaa agaggggctc    540

atccggccac cgtctgaagc tgaaatgaat gctgcccaaa ctgctgcctt tgtgaagatt    600

acaaaggcca gggcacaatc caacgacttt gccagcctag atgcagctgt cactcgaggt    660

cgtatcactg gaacaacaac cgctgaggct gttgtcactc taccaccacc ataa          714
```

<210> SEQ ID NO 17
<211> LENGTH: 237
<212> TYPE: PRT
<213> ORGANISM: Artificial Sequence
<220> FEATURE:
<223> OTHER INFORMATION: PVX capsid protein

<400> SEQUENCE: 17

```
Met Ser Ala Pro Ala Ser Thr Thr Gln Pro Ile Gly Ser Thr Thr Ser
1               5                   10                  15

Thr Thr Thr Lys Thr Ala Gly Ala Thr Pro Ala Thr Ala Ser Gly Leu
            20                  25                  30

Phe Thr Ile Pro Asp Gly Asp Phe Phe Ser Thr Ala Arg Ala Ile Val
        35                  40                  45

Ala Ser Asn Ala Val Ala Thr Asn Glu Asp Leu Ser Lys Ile Glu Ala
    50                  55                  60

Ile Trp Lys Asp Met Lys Val Pro Thr Asp Thr Met Ala Gln Ala Ala
65                  70                  75                  80

Trp Asp Leu Val Arg His Cys Ala Asp Val Gly Ser Ser Ala Gln Thr
```

```
                85                  90                  95

Glu Met Ile Asp Thr Gly Pro Tyr Ser Asn Gly Ile Ser Arg Ala Arg
            100                 105                 110

Leu Ala Ala Ala Ile Lys Glu Val Cys Thr Leu Arg Gln Phe Cys Met
        115                 120                 125

Lys Tyr Ala Pro Val Val Trp Asn Trp Met Leu Thr Asn Asn Ser Pro
    130                 135                 140

Pro Ala Asn Trp Gln Ala Gln Gly Phe Lys Pro Glu His Lys Phe Ala
145                 150                 155                 160

Ala Phe Asp Phe Phe Asn Gly Val Thr Asn Pro Ala Ala Ile Met Pro
                165                 170                 175

Lys Glu Gly Leu Ile Arg Pro Pro Ser Glu Ala Glu Met Asn Ala Ala
            180                 185                 190

Gln Thr Ala Ala Phe Val Lys Ile Thr Lys Ala Arg Ala Gln Ser Asn
        195                 200                 205

Asp Phe Ala Ser Leu Asp Ala Ala Val Thr Arg Gly Arg Ile Thr Gly
    210                 215                 220

Thr Thr Thr Ala Glu Ala Val Val Thr Leu Pro Pro Pro
225                 230                 235


<210> SEQ ID NO 18
<211> LENGTH: 216
<212> TYPE: PRT
<213> ORGANISM: Artificial Sequence
<220> FEATURE:
<223> OTHER INFORMATION: deleted PVX capsid protein

<400> SEQUENCE: 18

Met Cys Ala Thr Pro Ala Thr Ala Ser Gly Leu Phe Thr Ile Pro Asp
1               5                   10                  15

Gly Asp Phe Phe Ser Thr Ala Arg Ala Ile Val Ala Ser Asn Ala Val
            20                  25                  30

Ala Thr Asn Glu Asp Leu Ser Lys Ile Glu Ala Ile Trp Lys Asp Met
        35                  40                  45

Lys Val Pro Thr Asp Thr Met Ala Gln Ala Ala Trp Asp Leu Val Arg
    50                  55                  60

His Cys Ala Asp Val Gly Ser Ser Ala Gln Thr Glu Met Ile Asp Thr
65                  70                  75                  80

Gly Pro Tyr Ser Asn Gly Ile Ser Arg Ala Arg Leu Ala Ala Ala Ile
                85                  90                  95

Lys Glu Val Cys Thr Leu Arg Gln Phe Cys Met Lys Tyr Ala Pro Val
            100                 105                 110

Val Trp Asn Trp Met Leu Thr Asn Asn Ser Pro Pro Ala Asn Trp Gln
        115                 120                 125

Ala Gln Gly Phe Lys Pro Glu His Lys Phe Ala Ala Phe Asp Phe Phe
    130                 135                 140

Asn Gly Val Thr Asn Pro Ala Ala Ile Met Pro Lys Glu Gly Leu Ile
145                 150                 155                 160

Arg Pro Pro Ser Glu Ala Glu Met Asn Ala Ala Gln Thr Ala Ala Phe
                165                 170                 175

Val Lys Ile Thr Lys Ala Arg Ala Gln Ser Asn Asp Phe Ala Ser Leu
            180                 185                 190

Asp Ala Ala Val Thr Arg Gly Arg Ile Thr Gly Thr Thr Thr Ala Glu
        195                 200                 205

Ala Val Val Thr Leu Pro Pro Pro
```

-continued

```
    210                 215


<210> SEQ ID NO 19
<211> LENGTH: 216
<212> TYPE: PRT
<213> ORGANISM: Artificial Sequence
<220> FEATURE:
<223> OTHER INFORMATION: deleted and mutated PVX capsid protein

<400> SEQUENCE: 19

Met Pro Gly Thr Pro Ala Thr Ala Ser Gly Leu Phe Thr Ile Pro Asp
1               5                   10                  15

Gly Asp Phe Phe Ser Thr Ala Arg Ala Ile Val Ala Ser Asn Ala Val
            20                  25                  30

Ala Thr Asn Glu Asp Leu Ser Lys Ile Glu Ala Ile Trp Lys Asp Met
        35                  40                  45

Lys Val Pro Thr Asp Thr Met Ala Gln Ala Ala Trp Asp Leu Val Arg
    50                  55                  60

His Cys Ala Asp Val Gly Ser Ser Ala Gln Thr Glu Met Ile Asp Thr
65                  70                  75                  80

Gly Pro Tyr Ser Asn Gly Ile Ser Arg Ala Arg Leu Ala Ala Ala Ile
                85                  90                  95

Lys Glu Val Cys Thr Leu Arg Gln Phe Cys Met Lys Tyr Ala Pro Val
            100                 105                 110

Val Trp Asn Trp Met Leu Thr Asn Asn Ser Pro Pro Ala Asn Trp Gln
        115                 120                 125

Ala Gln Gly Phe Lys Pro Glu His Lys Phe Ala Ala Phe Asp Phe Phe
    130                 135                 140

Asn Gly Val Thr Asn Pro Ala Ala Ile Met Pro Lys Glu Gly Leu Ile
145                 150                 155                 160

Arg Pro Pro Ser Glu Ala Glu Met Asn Ala Ala Gln Thr Ala Ala Phe
                165                 170                 175

Val Lys Ile Thr Lys Ala Arg Ala Gln Ser Asn Asp Phe Ala Ser Leu
            180                 185                 190

Asp Ala Ala Val Thr Arg Gly Arg Ile Thr Gly Thr Thr Thr Ala Glu
        195                 200                 205

Ala Val Val Thr Leu Pro Pro Pro
    210                 215


<210> SEQ ID NO 20
<211> LENGTH: 651
<212> TYPE: DNA
<213> ORGANISM: Artificial Sequence
<220> FEATURE:
<223> OTHER INFORMATION: nucleotide sequence encoding deleted and
      mutated PVX capsid protein

<400> SEQUENCE: 20

atgcccggga ctcctgccac agcttcaggc ctgttcacca tcccggatgg ggatttcttt      60

agtacagccc gtgccatagt agccagcaat gctgtcgcaa caaatgagga cctcagcaag     120

attgaggcta tttggaagga catgaaggtg cccacagaca ctatggcaca ggctgcttgg     180

gacttagtca gacactgtgc tgatgtagga tcatccgctc aaacagaaat gatagataca     240

ggtccctatt ccaacggcat cagcagagct agactggcag cagcaattaa agaggtgtgc     300

acacttaggc aattttgcat gaagtatgct ccagtggtat ggaactggat gttaactaac     360

aacagtccac ctgctaactg gcaagcacaa ggtttcaagc ctgagcacaa attcgctgca     420
```

-continued

| | |
|---|---|
| ttcgacttct tcaatggagt caccaaccca gctgccatca tgcccaaaga ggggctcatc | 480 |
| cggccaccgt ctgaagctga aatgaatgct gcccaaactg ctgcctttgt gaagattaca | 540 |
| aaggccaggg cacaatccaa cgactttgcc agcctagatg cagctgtcac tcgaggtcgt | 600 |
| atcactggaa caacaaccgc tgaggctgtt gtcactctac caccaccata a | 651 |